US012779112B2

(12) United States Patent
Goudarzi

(10) Patent No.: US 12,779,112 B2
(45) **Date of Patent: *Nov. 3, 2026**

(54) INFILTRATION CANNULA WITH DUAL ANGLE CONFIGURATION

(71) Applicant: KG SURGICAL INSTRUMENTS LLC, Wrightsville Beach, NC (US)

(72) Inventor: Kamran Goudarzi, Wrightsville Beach, NC (US)

(73) Assignee: KG SURGICAL INSTRUMENTS LLC, Wrightsville Beach, NC (US)

( * ) Notice: Subject to any disclaimer, the term of this patent is extended or adjusted under 35 U.S.C. 154(b) by 377 days.

This patent is subject to a terminal disclaimer.

(21) Appl. No.: 18/581,085

(22) Filed: Feb. 19, 2024

(65) Prior Publication Data

US 2024/0189506 A1 Jun. 13, 2024

Related U.S. Application Data

(63) Continuation-in-part of application No. 17/316,403, filed on May 10, 2021, now Pat. No. 11,904,152.

(51) Int. Cl.

| | |
|---|---|
| ***A61M 5/152*** | (2006.01) |
| ***A61M 5/158*** | (2006.01) |
| ***A61M 25/00*** | (2006.01) |
| *A61B 18/14* | (2006.01) |

(52) U.S. Cl.

CPC ........ *A61M 5/158* (2013.01); *A61M 25/0068* (2013.01); *A61B 18/14* (2013.01)

(58) Field of Classification Search

CPC .............. A61M 5/158; A61M 25/0068; A61M 5/3291; A61M 2025/0687; A61M 5/3286; A61B 18/14; A61B 17/00008; A61B 2017/3413; A61B 2090/3925

See application file for complete search history.

(56) References Cited

U.S. PATENT DOCUMENTS

| | | | | |
|---|---|---|---|---|
| 5,758,665 | A | 6/1998 | Suval | |
| 5,817,050 | A | 10/1998 | Klein | |
| 6,375,648 | B1 * | 4/2002 | Edelman | A61M 3/0279 604/542 |
| 6,524,300 | B2 | 2/2003 | Meglin | |
| 6,613,026 | B1 | 9/2003 | Palasis et al. | |
| 6,685,666 | B1 | 2/2004 | Fontenot | |
| 6,692,473 | B2 | 2/2004 | St. Cyr et al. | |

(Continued)

*Primary Examiner* — Bhisma Mehta

*Assistant Examiner* — Fatimata Sahra Diop

(74) *Attorney, Agent, or Firm* — Invention To Patent Services; Alex Hobson

(57) ABSTRACT

A blunt-tipped cannula needle for injection of fluid into a subcutaneous tissue around a vein. The cannula needle includes a tubular side wall having three straight sections, each having a central axis. A second central axis of the central axes is angled away from a first central axis of the central axes at a first preselected angle in a first plane. A third central axis of the central axes is angled away from the second central axis at a combination of a preselected second angle and a preselected third angle, such that the third central axis is effectively angled away from the second central axis both at the second angle in the first plane and at the third angle in a second plane perpendicular to the first plane. A plurality of apertures in a distal end section of the needle that face the second central axis.

20 Claims, 10 Drawing Sheets

(56) References Cited

U.S. PATENT DOCUMENTS

| | | | | |
|---|---|---|---|---|
| 6,706,026 | B1 | 3/2004 | Goldstein et al. | |
| 6,916,292 | B2 | 7/2005 | Morwaski et al. | |
| 6,969,373 | B2 | 11/2005 | Schwartz et al. | |
| 7,056,315 | B2 | 6/2006 | Gonon et al. | |
| 7,297,094 | B2 | 11/2007 | Starkey et al. | |
| 7,465,291 | B2 | 12/2008 | Massengale | |
| 7,524,316 | B2 | 4/2009 | Hennings et al. | |
| 7,914,504 | B2 | 3/2011 | Klein | |
| 8,105,210 | B2 | 1/2012 | Klein | |
| 8,109,952 | B2 | 2/2012 | Pikus et al. | |
| 8,246,587 | B2 | 8/2012 | Klein | |
| 8,435,236 | B2 | 5/2013 | Mizrahi et al. | |
| 8,529,541 | B2 | 9/2013 | Klein | |
| 8,864,741 | B2 | 10/2014 | Lilley | |
| 9,838,478 | B2 | 12/2017 | Meng et al. | |
| 10,201,732 | B2 | 2/2019 | Mirza et al. | |
| 11,904,152 | B2 * | 2/2024 | Goudarzi | A61M 5/3286 |
| 2007/0129719 | A1 * | 6/2007 | Kendale | A61B 1/00096 606/41 |
| 2010/0174183 | A1 | 7/2010 | Schwartz et al. | |
| 2013/0123706 | A1 | 5/2013 | Genau et al. | |
| 2013/0324968 | A1 * | 12/2013 | Klein | A61M 5/158 604/513 |
| 2018/0264201 | A1 * | 9/2018 | Weksel | A61M 5/3286 |

* cited by examiner

INFILTRATION CANNULA WITH DUAL ANGLE CONFIGURATION

CROSS REFERENCE TO RELATED APPLICATIONS

This application claims the benefit of priority to U.S. patent application Ser. No. 17/316,403, filed on May 10, 2021 and currently pending; the entirety of which is incorporated by reference herein.

FIELD OF THE INVENTION

The present invention relates generally to a blunt-tipped cannula needle with a dual angle configuration. The present invention further relates to a surgical infiltration cannula with a blunt-tipped tubular needle, wherein the tubular needle has a dual angle configuration.

BACKGROUND OF THE INVENTION

In humans, varicose veins are twisted, enlarged veins that generally have deformed valves and abnormal blood flow when compared to a normal, healthy vein. Any superficial vein on the human body may become varicosed, however the veins most commonly affected are those in the legs, since standing and walking upright increases the pressure in the veins of the lower body. The constant pressure in the veins of the lower body over the lifetime may result in valve deformation and deformity in what were previously normal veins. Varicose veins in the leg may be solely a cosmetic concern or can cause significant pain and discomfort. Weak or damaged valves in the superficial veins of the leg can lead to varicose veins. If the valves are weak or damaged, blood can flow backward through the vein and pool in the vein, which can result in stretching or twisting of the vein. If left untreated, varicose veins may lead to more serious medical problems, such as such as swelling and inflammation of the vein or leg ulcers.

One current surgical technique for dealing with the problem of varicose veins is to remove varicose veins by using ablation, which is the removal of such veins through vaporization of the varicose vein or other erosive process. At the present time, varicose veins are ablated using different surgical techniques. For example, two common techniques utilized in the ablation of varicose veins are radiofrequency ablation and laser ablation. In such surgical techniques, radiofrequency energy or laser energy are used to burn and close the abnormal varicose veins using fibers inserted into the faulty vein, which fibers are then used to burn and seal the varicosed vein.

Two of the most common veins in the leg that become varicosed and need to be removed through ablation are the great saphenous vein and the small saphenous vein. The great saphenous vein is the longest vein in the human body, running along the length of the lower leg. Ablation of the great saphenous vein is often only performed in the area of the leg from the knee to the hip. During vein ablation surgery, any connective tissue or other tissues that remain attached to the vein can transfer heat from the laser into tissue surrounding the vein, causing damage to the surrounding tissues. This transfer of heat can result in significant damage to the surrounding tissue. The reason that the region of the leg from the knee down to the ankle is often avoided by surgeons in varicose vein ablation is due to the position of the saphenous nerve, which accompanies the great saphenous vein. The saphenous nerve is the largest cutaneous branch of the femoral nerve. The saphenous nerve is a sensory nerve, which means that injury to this nerve can result in loss of sensation or sensory irregularity in the medial leg. In addition, any nerve injury can result in neuritis, leading to the possibility of significant pain, permanent paresthesia, or permanent hyperesthesia.

Similar issues present themselves for surgeons performing ablations of the small saphenous vein, due to the position of the sural nerve. The small saphenous vein is a relatively large superficial vein of the posterior leg. The sural nerve is a sensory nerve in the calf region of the leg that provides sensation to the skin of the lateral foot and lateral lower ankle. The sural nerve usually gets very close to the small saphenous vein about mid-calf. Many surgeons avoid performing ablations on the small saphenous vein below the mid-calf region, limiting ablations from the region from the mid-calf to the knee, in order to avoid damaging the sural nerve. Unfortunately, the small saphenous vein can become incompetent below the mid-calf, feeding numerous vein tributaries including the gastrocnemius perforator veins. Perforator veins perforate the deep fascia of muscles, connecting the superficial veins to the deep veins.

Both laser ablation and radiofrequency ablation require the injection of tumescence anesthesia around the vein in order to numb the vein prior to ablation. Tumescent anesthesia, which is commonly used in the treatment of varicose veins prior to the ablation procedure, is a mixture of an anesthetic compound such as lidocaine and epinephrine, which is added to induce vasoconstriction, which is well known in the art.

Human veins are often surrounded by a continuous sheet of connective tissue known as the fascia. During the ablation of varicose veins, tumescent anesthesia is often injected into and contained within the fascia surrounding the vein prior to the vein ablation procedure in order to numb the vein and to prepare it for ablation. The tumescent anesthesia is often injected into the fascia in multiple locations using a straight thin-walled cannula. Current ablation procedures for varicose veins often require several perforations through the skin to enable access to the fascia surrounding the vein. During the procedure, the tumescent anesthesia is usually injected into and contained within the fascia or other tissue surrounding the varicose vein at multiple locations along the length of the vein.

One current method of infiltration of local anesthetic into the varicose vein fascia is through the use of a blunt tipped infiltration cannula. The injection needles of these cannulas are constructed out of rigid stainless steel and typically have round or oval cross-sections, with apertures distributed about the distal end of the cannula. The apertures are distributed over about 15% or 25% or less than 5.0 cm of the distal end of the cannula. The current practice generally requires from 5 to 15 points of injection through small incisions in the skin and into the fascia, depending on the length of the vein in order to anesthetize the entire vein. The more points of injection through the skin and fascia, the more pain and discomfort that a patient will experience during the vein ablation procedure. These traditional infiltration cannulas are intended to be inserted through the incisions in the skin and then moved in and out through the subcutaneous tissue while tumescent anesthesia is ejected through the distal apertures of the cannula.

Various variations to infiltration cannulas have been used in other areas of surgery, such as liposuction surgery. These cannulas include simple geometric changes to the standard straight infiltration cannula. Such cannulas include simple curves and single or double angled configurations, all of which are generally angled such that the curves and angles are all within the same plane, such that the device has overall geometry of the cannula remains essentially planar in form.

Another type of infiltration cannula used is a sharp tipped tumescent infiltration cannula, which generally uses a long sharp needle similar to a spinal needle. The tumescent anesthesia is injected into the subcutaneous tissue by moving the needle in and out of the subcutaneous tissue along paths that radiate from the skin puncture site along the vein.

Unfortunately, the cannulas and associated surgical techniques currently being used for the ablation of varicose veins increase the risk of perforation of the vein wall of the varicose vein being treated. Varicose veins walls are at higher risk for perforation because the process of becoming varicosed often results in the wall of the varicose vein being structurally weakened as a result of their altered and dysfunctional physical condition. Such perforation of vein walls increases the risk that the straight and relatively short cannulas currently used for injection of tumescent anesthesia in the area around varicose veins will accidentally penetrate the vein itself, rather than the fascia and other tissue surrounding the vein. If the cannula accidentally enters the vein, a bolus of tumescent anesthesia may be accidentally injected into the vein. The injection of such a bolus containing lidocaine and epinephrine can potentially be harmful to the patient, potentially resulting in hemodynamic instability, including tachycardia, bradycardia, irregular heartbeat, and other possible complications, including the possibility of death.

In performing ablation of varicose veins, in addition to numbing the vein prior to ablation for patient comfort, the vein should be compressed as much as possible prior to the ablation procedure. While the injection of the tumescent anesthesia into the facia using current cannulas and associated techniques for the injection of tumescent anesthesia does result in compression of the vein, the vein is normally only partially compressed, resulting in a significant amount of blood remaining in the vein during the ablation procedure itself. The blood that is left in the vein during the laser ablation procedure can result in patients experiencing the taste of "burnt blood," the underlying psychological mechanism for which is currently unknown. This is another unpleasant side effect of the ablation of varicose veins.

Therefore, there is a need for a novel cannula device and associated surgical technique for the ablation of varicose veins that decreases the need for excessive incisions into the skin and fascia. Such a cannula and associated surgical technique should enable as much of the varicose vein as possible to be separated from its surrounding tissue prior to ablation, particularly including any surrounding skin and nerves. In addition, the cannula and technique should reduce any damage to any tissue surrounding the varicose vein as much as possible, particularly nerves, such as the saphenous nerve, the sural nerve, and the skin. The cannula and technique should also permit better closure of the vein and a lower recurrence rate of varicose veins. The varicose vein should be compressed as much as possible to eliminate as much blood from the vein prior to the ablation procedure. In addition, the cannula needs to be blunt rather than sharp to avoid causing damage to the nerve lining of any surrounding nerves.

SUMMARY OF THE INVENTION

The present invention addresses the needs discussed above, identified below, and those that are known in the art. The present invention is directed to improvements in surgical cannula needles and surgical infiltration cannulas such as those used to inject tumescent anesthesia into the tissue surrounding varicose veins.

In an exemplary embodiment of the present invention, a tubular needle of a surgical cannula for injection of fluid into the subcutaneous tissue around a vein comprises a proximal end, the proximal end being open and capable of being in fluid communication with a source of fluid. The tubular needle further comprises a distal end, the distal end comprising a closed blunt tip. The tubular needle further comprises a tubular side wall defining a hollow central lumen. The hollow central lumen extends from the proximal end to the closed blunt tip at distal end. The hollow central lumen is capable of being in fluid communication with the source of fluid.

The tubular side wall further comprises a first proximal end section. The first proximal end section comprises a first straight section extending from the proximal end. The first straight section has a length in the range of about 0.5 cm to about 5.5 cm, or from about 1 cm to about 5.5 cm, or about 2 cm to about 5.5 cm, or about 3.0 cm to about 5.5 cm, or about 4.0 cm to about 5.5 cm. The first straight section further has a first central axis.

The tubular side wall further comprises a second main body section extending from the first proximal end section. The second main body section comprises a second straight section. The second straight section has a length in the range of about 10.0 cm to about 60.0 cm, or from about 20 cm to 60 cm, or a from about 30 cm to 60 cm, or from about 40 cm to about 60 cm. The second straight section further has a second central axis. The second central axis is angled away from the first central axis at a first angle in a first plane, such that the first central axis and the second central axis are coplanar in the first plane. The first angle is an acute angle, less than 90° or from about 15° to about 65°, or from about 25° to about 55°, and preferably in the range of about 35° to about 45°. Too large of a first acute angle may result in too much rotation of the second straight section and too small of a first acute angle may be more difficult to rotate the tubular needle.

The tubular side wall further comprises a third distal end section. The third distal end section extends from the second main body section to the closed blunt tip. The third distal end section comprises a third straight section. The third straight section has a length in the range of 1 cm to about 6 cm, or from about 1 cm to about 5 cm, and preferably for most procedures of about 1.0 cm to about 3.0 cm, or any other range between and including the length values provided. The third straight section further has a third central axis. The third central axis is angled away from the second central axis at a fourth composite angle. The fourth composite angle is a combination of a second angle and a third angle, such that the third central axis is effectively angled away from the second central axis both at the second angle in the first plane and at the third angle in a second plane. The second plane is perpendicular to the first plane such that second central axis is located on a line of intersection of the first plane and the second plane. The second angle is an acute angle, less than 90° and preferably from about 10° to about 55°, or from about 10° to about 45°, and most preferably in the range of about 15° to about 35°, and the third angle is an acute angle, less than 90° and preferably from about 10° to about 45°, or from about 10° to about 35°, and most preferably in the range of about 15° to about 25°, such that the fourth composite angle is an acute angle, less than 90° and from about 10° to about 65°, or from about 15° to about 50°, and most preferably in the range of about 20.8° to about 40°. The third central axis is not coplanar with the first central axis. The length of the second straight section is much longer than the length of the first straight section and the length of the third straight section to enable access to the treatment location for injection of tumescent and to enable rotation of the blunt tip around a vein. The length of the second straight section may be a factor greater in length than the length of the first straight section and/or the length of the third straight section, such as about 2 times or more, about 3 times or more, about four times or more, about 5 times or more, about 6 times or more, about 7 times or more, about 8 times or more, about 10 times or more and any range between and including the factors provided.

The third distal end section further comprises an aperture of in some cases a plurality of apertures. The aperture(s) are defined by the tubular side wall and extend from the hollow central lumen to a section of an exterior surface of the third straight section that a face the second central axis wherein fluid ejected through the aperture(s) is directed toward the second central axis, or within about 25° and preferably within 15° and even more preferably within 10° and most preferably within 5° of the second central axis. Tumescent ejected from the apertures that substantially face the second central axis is ejected away from the vein during a varicose vein procedure. Put another way, an aperture faces or substantially faces the second central axis when a line from the third central axis through the aperture extends within about 25° and preferably within 15° and even more preferably within 10° and most preferably within 5° of the second central axis. The plurality of apertures are absent from a remaining section of the exterior surface of the third straight section that does not at least substantially face the second central axis. The plurality of apertures allow the source of fluid to be capable of being in fluid communication with an area external to the third straight section adjacent to the plurality of apertures.

In another exemplary embodiment of the present invention, a tubular needle of a surgical cannula for injection of fluid into the subcutaneous tissue around a vein comprises a proximal end, the proximal end being open and capable of being in fluid communication with a source of fluid. The tubular needle further comprises a distal end, the distal end comprising a closed blunt tip. The tubular needle further comprises a tubular side wall defining a hollow central lumen. The hollow central lumen extends from the proximal end to the closed blunt tip at distal end. The hollow central lumen is capable of being in fluid communication with the source of fluid.

The tubular side wall further comprises a first proximal end section. The first proximal end section comprises a first straight section extending from the proximal end. The first straight section may have length in the range of about 0.5 cm to about 5.5 cm. The first straight section further has a first central axis.

The tubular side wall further comprises a second main body section extending from the first proximal end section. The second main body section comprises a second straight section. The second straight section may have length in the range of about 10.0 cm to about 60.0 cm. The second straight section further has a second central axis. The second central axis is angled away from the first central axis at a first angle in a first plane, such that the first central axis and the second central axis are coplanar in the first plane. The first angle is an acute angle, less than 90° and preferably in the range of about 35° to about 45°.

The third distal end section extends from the second main body section to the closed blunt tip. The third distal end section comprises a third straight section. The third straight section may have a length in the range of about 4.0 cm to about 6.0 cm. The third straight section further has a third central axis. The third central axis is angled away from the second central axis at a fourth composite angle. The fourth composite angle is a combination of a second angle and a third angle, such that the third central axis is effectively angled away from the second central axis both at the second angle in the first plane and at the third angle in a second plane. The second plane is perpendicular to the first plane such that second central axis is located on a line of intersection of the first plane and the second plane. The second angle may be in the range of about 5° to about 15° and the third angle may be in the range of about 5° to about 15°, such that the fourth composite angle may be in the range of about 7.1° to about 20.8°. The third central axis is not coplanar with the first central axis.

The third distal end section further comprises a plurality of apertures. The plurality of apertures are defined by the tubular side wall and extend from the hollow central lumen to a section of an exterior surface of the third straight section that at least substantially faces the second central axis. The plurality of apertures are absent from a remaining section of the exterior surface of the third straight section that does not at least substantially face the second central axis. The plurality of apertures allow the source of fluid to be capable of being in fluid communication with an area external to the third straight section adjacent to the plurality of apertures.

In another exemplary embodiment of the present invention, a surgical cannula for injection of fluid into the subcutaneous tissue around a vein comprises a proximal end, the proximal end being open and capable of being in fluid communication with a source of fluid. The surgical cannula further comprises a distal end, the distal end comprising a closed blunt tip. The surgical cannula further comprises a hollow central lumen extending from the proximal end to the closed blunt tip at the distal end. The hollow central lumen is capable of being in fluid communication with the source of fluid.

The surgical cannula further comprises a fluid connector extending from the proximal end. The fluid connector comprises a first side wall defining a first portion of the hollow central lumen located within the fluid connector. The fluid connector is open and capable of being in fluid communication with the source of fluid.

The surgical cannula further comprises a handle extending from the fluid connector. The handle comprises a second side wall defining a second portion of the hollow central lumen located within the handle. The hollow central lumen passes from the fluid connector through the handle.

The surgical cannula further comprises a tubular needle extending from the handle to the closed blunt tip at the distal end. The tubular needle comprises a third side wall defining a third portion of the hollow central lumen located within the tubular needle. The hollow central lumen passes from the handle through the tubular needle to the closed blunt tip.

The tubular needle further comprises a first proximal end section. The first proximal end section comprises a first straight section extending from the handle. The first straight section may have a length in the range of about 0.5 cm to about 5.5 cm. The first straight section has a first central axis. The first proximal end section further comprises a first curved transitional section extending from the first straight section.

The tubular needle further comprises a second main body section extending from the first curved transitional section. The second main body section comprises a second straight section. The second straight section may have a length in the range of about 10.0 cm to about 60.0 cm. The second straight section further has a second central axis. The second central axis is angled away from the first central axis at a first angle in a first plane, such that the first central axis and the second central axis are coplanar in the first plane. The first angle may be in the range of about 15° to about 65°, or about 25° to about 55°, and preferably about 35° to about 45°. This angle provides a handle orientation that is ergonomic for manipulating the tubular needle including rotation of the closed blunt tip on the distal end about a vein. If the angle is too great, rotation of the first straight section will cause too great of a rotational diameter of the closed blunt end. The second main body section further comprises a second curved transitional section extending from the second straight section.

The tubular needle further comprises a third distal end section. The third distal end section comprises a third straight section extending from the second curved transitional section to the closed blunt tip. The third straight section has a length in the range of about 1.0 cm to about 3.0 cm. The third straight section further has a third central axis. The third central axis is angled away from the second central axis at a fourth composite angle. The fourth composite angle is a combination of a second angle and a third angle, such that the third central axis is effectively angled away from the second central axis both at the second angle in the first plane and at the third angle in a second plane. The second plane is perpendicular to the first plane such that the second central axis is located on a line of intersection of the first plane and the second plane. The second angle is an acute angle, less than 90° and preferably in the range of about 15° to about 35° and the third angle is in the range of about 15° to about 25°, such that the fourth composite angle is in the range of about 20.8° to about 40°. The third central axis is not coplanar with the first central axis.

The tubular needle further comprises a plurality of apertures. The plurality of apertures are defined by the third side wall and extend from the hollow central lumen to a section of an exterior surface of the third straight section that at least substantially faces the second central axis. The plurality of apertures are absent from a remaining section of the exterior surface of the third straight section that does not at least substantially face the second central axis. The plurality of apertures allow the source of fluid to be capable of being in fluid communication with an area external to the third straight section adjacent to the plurality of apertures.

In another exemplary embodiment of the present invention, a surgical cannula for injection of fluid into the subcutaneous tissue around a vein comprises a proximal end, the proximal end being open and capable of being in fluid communication with a source of fluid. The surgical cannula further comprises a distal end, the distal end comprising a closed blunt tip. The surgical cannula further comprises a hollow central lumen extending from the proximal end to the closed blunt tip at the distal end. The hollow central lumen is capable of being in fluid communication with the source of fluid.

The surgical cannula further comprises a fluid connector extending from the proximal end. The fluid connector comprises a first side wall defining a first portion of the hollow central lumen located within the fluid connector. The fluid connector is open and capable of being in fluid communication with the source of fluid.

The surgical cannula further comprises a handle extending from the fluid connector. The handle comprises a second side wall defining a second portion of the hollow central lumen located within the handle. The hollow central lumen passes from the fluid connector through the handle.

The surgical cannula further comprises a tubular needle extending from the handle to the closed blunt tip at the distal end. The tubular needle comprises a third side wall defining a third portion of the hollow central lumen located within the tubular needle. The hollow central lumen passes from the handle through the tubular needle to the closed blunt tip.

The tubular needle further comprises a first proximal end section. The first proximal end section comprises a first straight section extending from the handle. The first straight section may have a length in the range of about 0.5 cm to about 5.5 cm. The first straight section has a first central axis. The first proximal end section further comprises a first curved transitional section extending from the first straight section.

The tubular needle further comprises a second main body section extending from the first curved transitional section. The second main body section comprises a second straight section. The second straight section may have a length in the range of about 10.0 cm to about 60.0 cm. The second straight section further has a second central axis. The second central axis is angled away from the first central axis at a first angle in a first plane, such that the first central axis and the second central axis are coplanar in the first plane. The first angle is an acute angle, less than 90° and preferably in the range of about 35° to about 45°. The second main body section further comprises a second curved transitional section extending from the second straight section.

The tubular needle further comprises a third distal end section. The third distal end section comprises a third straight section extending from the second curved transitional section to the closed blunt tip. The third straight section has a length in the range of about 4.0 cm to about 6.0 cm. The third straight section further has a third central axis. The third central axis is angled away from the second central axis at a fourth composite angle. The fourth composite angle is a combination of a second angle and a third angle, such that the third central axis is effectively angled away from the second central axis both at the second angle in the first plane and at the third angle in a second plane. The second plane is perpendicular to the first plane such that the second central axis is located on a line of intersection of the first plane and the second plane. The second angle may be in the range of about 5° to about 15° and the third angle may be in the range of about 5° to about 15°, such that the fourth composite angle is in the range of about 7.1° to about 20.8°. The third central axis is not coplanar with the first central axis.

The tubular needle further comprises a plurality of apertures. The plurality of apertures are defined by the third side wall and extend from the hollow central lumen to a section of an exterior surface of the third straight section that at least substantially faces the second central axis. The plurality of apertures are absent from a remaining section of the exterior surface of the third straight section that does not at least substantially face the second central axis. The plurality of apertures allow the source of fluid to be capable of being in fluid communication with an area external to the third straight section adjacent to the plurality of apertures.

The tubular needle of a surgical cannula as described herein, may be used in ventriculoperitoneal shunt procedures. When the pressure of cerebral spinal fluid in the brain is high, neurosurgeons will place a shunt in the brain tunnel through the subcutaneous tissue all the way down from the base of the skull and neck to below the diaphragm and connect to the peritoneal cavity so that the fluid drains from the brain into the abdomen. The tubular needle, as described herein, may be used for creating a pathway and locating the shunt from said base of the skull to the abdomen. The tubular needle for this procedure may include two lumens, a first lumen to pass a snare tether coupled to a snare, to couple with a shunt tether and a second lumen for fiberoptic light to show where the distal end of the tubular needle is located. The light may be visible through the tissue of the person and rotation of the tubular needle may increase or decrease the intensity of light detected through the person's tissue, thereby providing awareness of the orientation of the third straight section and blunt tip. Also, one of the lumens may be used for hydrodissection wherein a fluid, such as water or water and saline, is used to separate tissue to aid in passage of the tubular needle from the neck to the abdomen. The tubular needle is inserted into a person's body proximal to the neck and passed down into the abdomen, where the snare is coupled with a shunt tether. The tubular needle is then pulled back through the body to pull the shunt tether from the abdomen or peritoneal cavity back up to the neck. The ventriculoperitoneal shunt can then be pulled by the shunt tether into the abdomen and configured in the peritoneal cavity. The ventriculoperitoneal shunt may be configured in or along a catheter for passage from the neck to the abdomen and the catheter may be a peel-away catheter, when the ventriculoperitoneal shunt is configured therein, that is configured to split along the length for removal while leaving the ventriculoperitoneal shunt in place. The light device produces a light that enables identification of the orientation and location of the blunt tip of the tubular needle. The first proximal end section of the tubular needle can be rotated to rotate the third distal end section and the blunt tip as the tubular needle is traversed down from the neck to the abdomen. The blunt tip, and/or the third straight section of the tubular needle may be detachably attachable to the tubular needle which may enable attachment of a tip that is more conducive for penetration of the peritoneal cavity, wherein the tip may taper to the distal end for easier puncturing capability. The blunt tip may be passed through the skin and the blunt tip may be exchanged for a tapering tip before the distal end is again inserted into the abdomen and then passed into the peritoneal cavity.

An exemplary tubular needle of a surgical cannula as described herein, may be used for delivery of anesthesia during a liposuction procedure, The tubular needle may include two lumens as detailed herein. A first lumen may have a plurality of apertures for delivery of the anesthesia and the second lumen may retain a light device and light tether for providing power to the light device.

Other features and advantages of the present invention will be apparent from the following more detailed description of the preferred embodiment, taken in conjunction with the accompanying drawings which illustrate, by way be example, the principles of the invention.

DETAILED DESCRIPTION OF THE ILLUSTRATED EMBODIMENTS

As described in further detail below, the present invention is a novel tubular surgical cannula needle utilizing a dual angle configuration, taking advantage of the use of tumescent anesthesia in order to provide the infiltration of tumescent anesthesia into the area surrounding varicose veins, in order to prepare such veins for ablation. The present invention is also a novel surgical infiltration cannula that includes a tubular needle utilizing the dual angle configuration. The purpose of the surgical infiltration cannula and tubular needle of the present invention is to permit the injection of tumescent anesthesia in the area around a varicose vein, such as those found in the human leg, for the purpose of preparing both the patient and the varicose vein itself for the ablation of the varicose vein.

Ranges disclosed herein are inclusive and independently combinable (e.g., ranges of "about 5 cm to about 10 cm" is inclusive of all the endpoints and all intermediate values of the ranges of "about 5 cm to about 10 cm," etc.) The modifier "about" used in connection with a quantity is inclusive of the stated value and has meaning dictated by the context, (e.g. includes the degree of error associated with measurement of the particular quantity). For example, a quantitative value indicated as being about a number may vary by +10%.

The term "comprising" (and its grammatical variations), as used herein, is used in the inclusive sense of "having" or "including" and not in the exclusive sense of "consisting only of."

The terms "proximal" and "distal" as used herein are used to represent two preselected ends of the surgical cannula and cannula needle of the present invention. The terms "proximal" and "distal" are only used as terms of geometric orientation with respect to the overall geometry of the elements of the surgical cannula and tubular cannula needle. The same is true for the terms "proximal end section" and "distal end section" as used herein, which represent two preselected end sections of the tubular cannula needle of the present invention. The terms "proximal end section" and "distal end section" are only used as terms of geometric orientation with respect to the elements of the tubular cannula needle.

The terms "first reference plane," "first plane," "second reference plane," and "second plane" as used herein refer to two preselected perpendicular geometric planes used as reference planes to describe the three-dimensional configuration of the surgical infiltration cannula and tubular cannula needle of the present invention as further set forth herein. These planes are not shown in the figures herein as they are not physical components of the present invention, rather the angulation of elements of the invention in the two planes of reference are shown in the figures herein.

Figure 1:
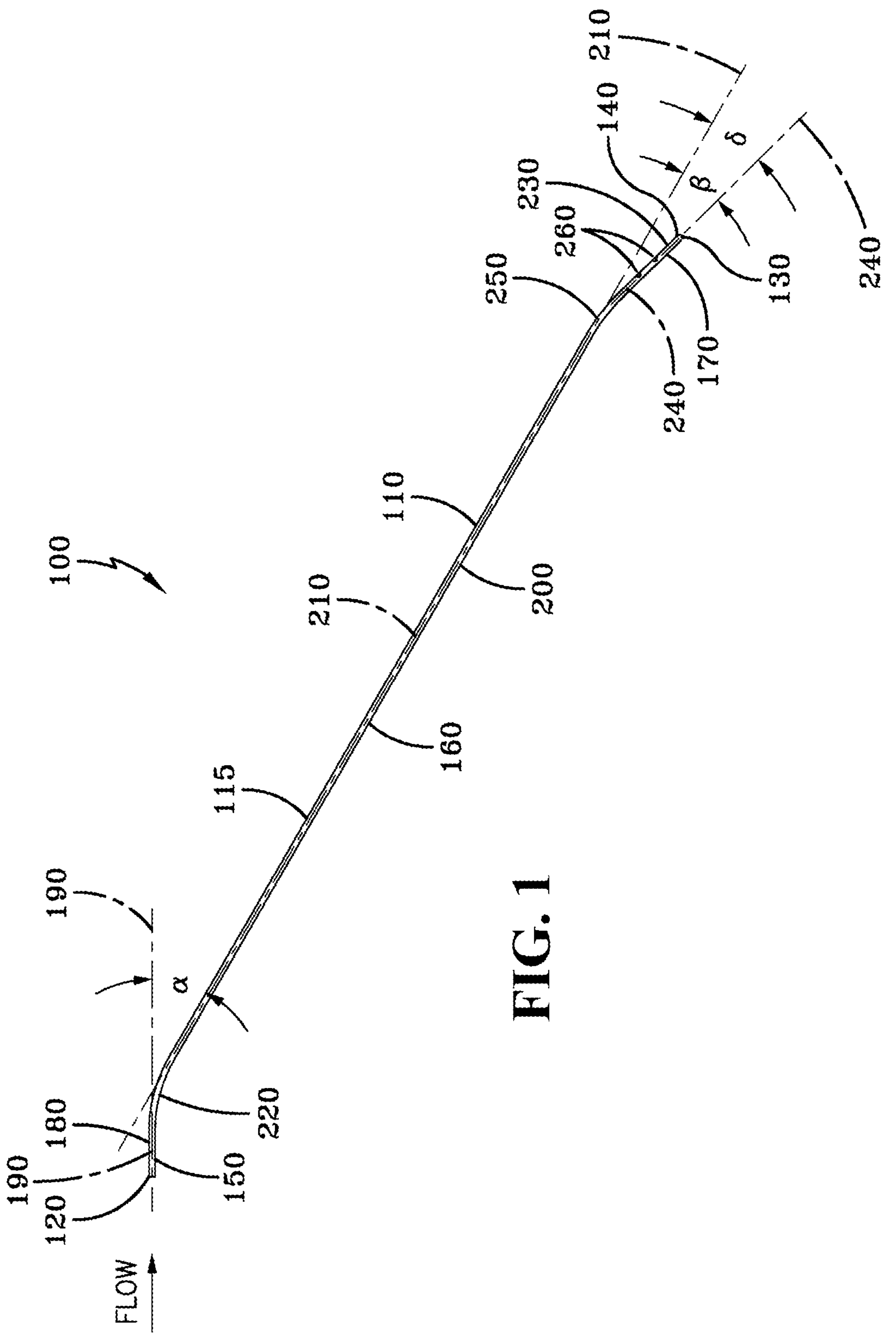
FIG. 1 is a side view of a cannula needle of the present invention.

As set forth herein, the side view of FIG. 1 of an embodiment of the cannula needle of the present invention is a view facing the first reference plane, such that the angulation of elements in the first reference plane is shown. The top view of FIG. 2, which the embodiment of the cannula needle of the present invention shown in FIG. 1, is a view facing the second reference plane, such that the angulation of elements in the second reference plane is shown.

Figure 2:
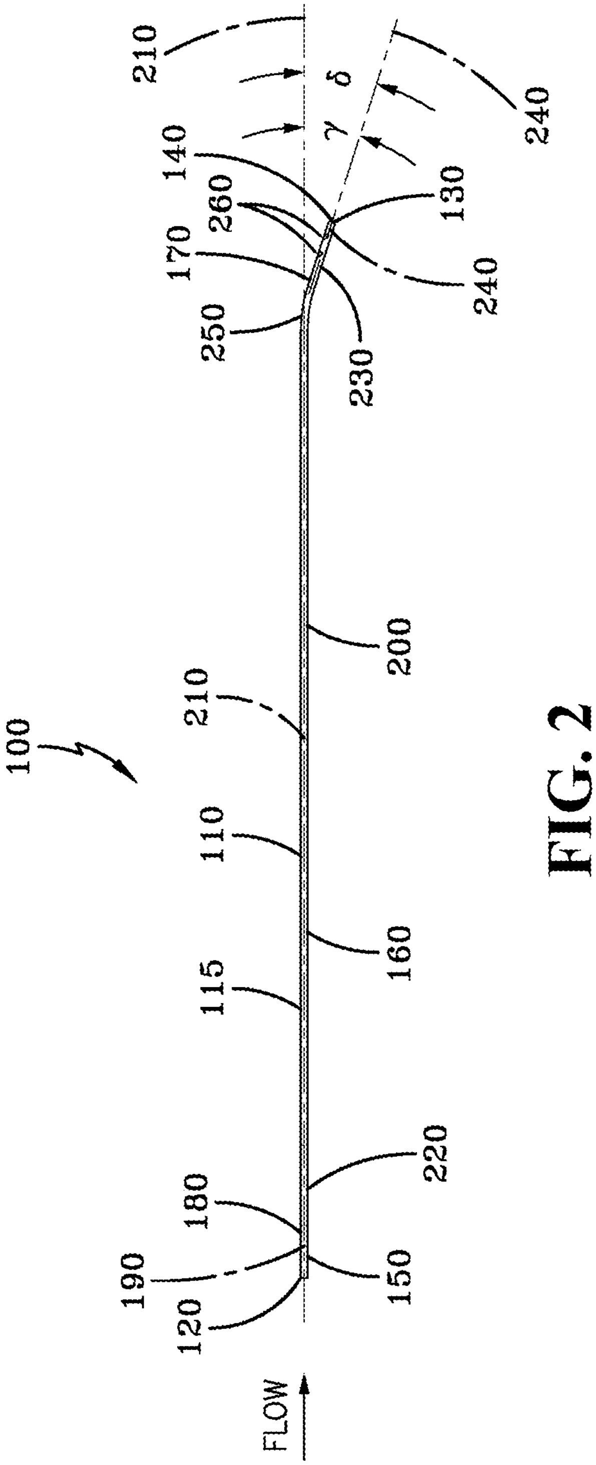
FIG. 2 is a top view of the cannula needle shown in FIG. 1.

As shown in FIG. 1 and FIG. 2, the cannula needle 100 has a tubular side wall 110 that comprises the body of the cannula needle 100. The tubular sidewall 110 has an exterior surface 115. The cannula needle 100 has a proximal end 120 and a distal end 130. The tubular sidewall 110 defines a hollow central lumen (not shown in FIG. 1 and FIG. 2) of the cannula needle 100 that is capable of being in fluid communication with a source of fluid and that extends from the proximal end 120 to the distal end 130. The proximal end 120 is open which allows the hollow central lumen to be capable of being in fluid communication with a source of fluid. The tubular sidewall 110 has three main sections, a first proximal end section 150, a second main body section 160, and a third distal end section 170.

The first proximal end section 150 has a first straight section 180. The first straight section 180, being tubular, has a first central axis 190. The length of the first straight section 180 is in the range of about 0.5 cm to about 5.5. cm. In a more preferred embodiment, the length of the first straight section 180 is in the range of about 1.0 cm to about 4.0 cm. In a more preferred embodiment, the length of the first straight section 180 is about 3.5 cm. In an alternate embodiment, the length of the first straight section 180 is about 2.0 cm. In another alternate embodiment, the length of the first straight section 180 is about 1.0 cm. The length of the second straight section 200 is much longer than the length of the first straight section 190 and the length of the third straight 230 section to enable access to the treatment location for injection of tumescent from the plurality of apertures 260 in the third straight section 230, and to enable rotation of the blunt tip 140 around a vein. The length of the second straight section may be a factor greater in length than the length of the first straight section and/or the length of the third straight section, such as about 2 times or more, about 3 times or more, about four times or more, about 5 times or more, about 6 times or more, about 7 times or more, about 8 times or more, about 10 times or more and any range between and including the factors provided. As shown in FIG. 1, the length of the second straight section 200 is more than double the length of the e first straight section 190 and the length of the third straight 230 and is more than 7 times greater in length that the first straight section 190 and the length of the third straight 230.

The second main body section 160 extends from the first proximal end section 150 and has a second straight section 200. The second straight section 200, being tubular, has a second central axis 210. The length of the second straight section 200 is in the range of about 10.0 cm to about 60.0 cm. In one embodiment of the present invention, the length of the second straight section 200 is about 10.0 cm. In another embodiment of the present invention, the length of the second straight section 200 is about 20.0 cm. In another embodiment of the present invention, the length of the second straight section 200 is about 30.0 cm. In another embodiment of the present invention, the length of the second straight section 200 is about 40.0 cm. In another embodiment of the present invention, the length of the second straight section 200 is about 45.0 cm. In another embodiment of the present invention, the length of the second straight section 200 is about 50.0 cm. In another embodiment of the present invention, the length of the second straight section 200 is about 60.0 cm.

In a preferred embodiment, the first proximal end section 150 further comprises a first curved transitional section 220 extending from the first straight section 180, with the second straight section 200 extending from first curved transitional section 220. Such curvature avoids the use of sharp corners to prevent damage to the tissue of the limb into which the cannula needle 100 is inserted. In a more preferred embodiment, the first curved transitional section 220 has a length in the range of about 0.4 cm to about 2.0 cm. In an even more preferred embodiment, the first curved transitional section 220 has a length of about 1.2 cm.

The cannula needle 100 of the present invention is intended for insertion through the skin of a limb of a person to permit the injection of tumescent anesthesia in the tissue around a vein. In the present invention, the second central axis 210 is angled away from the first central axis 190 at a preselected angle α in a first reference plane, such that the first central axis 190 and the second central axis 210 are coplanar in the first plane. The angle α is an acute angle as shown, less than 90° and preferably in the range of about 35° to about 45°. In a more preferred embodiment, the angle α is about 40°. Having the second central axis 210 angled away from the first central axis 190 at angle α permits a surgeon to readily adjust the position of the cannula needle 100 by manipulating the proximal end 120 of the cannula needle 100. Due to human anatomy, using the cannula needle 100 to inject tumescent anesthesia around a vein of any significant length requires that the third straight section 230 and at least a portion of the second straight section 200 be inserted under the skin of the limb through a small hole in the skin of the limb. As the distal end 130 of the cannula needle 100 is intended to be used to manipulate the position of the cannula needle 100 within the limb, the distal end 130 must remain outside of the limb to be readily repositioned by the surgeon. The angulation of the second central axis 210 with respect to the first central axis 190 permits the ready adjustment both the second straight section 200 and third straight section 230 during surgery. The geometry of the cannula needle 100 of the present invention therefore allows the distal end 130 of the cannula needle 100 to remain positioned away from the skin of the limb during surgical procedures.

The third distal end section 170 has a third straight section 230. The third straight section 230, being tubular, has a third central axis 240. In one embodiment of the present invention, the length of the third straight section 230 is in the range of about 1.0 cm to about 3.0 cm. In a more preferred embodiment of the present invention, the length of the third straight section 230 is about 2.0 cm.

In a preferred embodiment, the second main body section 160 further comprises a second curved transitional section 250 extending from the second straight section 200, with the third straight section 230 extending from the second curved transitional section 250. Such curvature avoids the use of sharp corners to prevent damage to the tissue of the limb into which the cannula needle 100 is inserted. In a more preferred embodiment, the second curved transitional section 250 has a length in the range of about 0.4 cm to about 1.2 cm. In an even more preferred embodiment, the second curved transitional section 250 has a length of about 0.8 cm.

As set forth herein, the line of intersection of the first reference plane and a second reference plane is congruent with the second central axis 210. The third central axis 240 is angled away from the second central axis 210 at a fourth composite angle δ, the fourth composite angle δ being a combination of a second preselected component angle β in the first plane and a third preselected component angle γ in the second plane. From a geometric standpoint, since the first plane and the second plane are perpendicular, the fourth composite angle δ is characterized as having two perpendicular angular components, angle β and angle γ. Thus, the geometric configuration of the first central axis 190, the second central axis 210, and the third central axis 240 of the present invention requires that the first central axis 190 not be coplanar with the third central axis 240.

In an embodiment of the present invention, when the third straight section 230 is in the range of about 1.0 cm to about 3.0 cm, the fourth composite angle δ is an acute angle as shown, less than 90° and preferably in the range of about 20.8° to about 40.0°, with the second component angle β being an acute angle as shown, less than 90° and preferably in the range of about 15° to about 35°, and with the third component angle γ being an acute angle as shown, less than 90° and preferably in the range of about 15° to about 25°. In a more preferred embodiment, the fourth composite angle δ is about 30.6°, with the second component angle β being about 25° and the third component angle γ being about 20°.

In an alternate embodiment of the present invention, the third straight section 230 has a length in the range of about 4.0 cm to about 6.0 cm. In this alternate embodiment, the fourth composite angle δ is in the range of about 7.1° to about 20.8°, with the second component angle β being in the range of about 5° to about 15° and the third component angle γ being in the range of about 5° to about 15°. In a more preferred alternate embodiment, the fourth composite angle δ is about 14.0°, with the second component angle β being about 10° and the third component angle γ being about 10°.

As FIG. 1 is a view of the cannula needle 100 of the present invention in the direction facing the first plane, only the second component angle β of fourth composite angle δ is visible in FIG. 1. Likewise, as FIG. 2 is a view of the cannula needle 100 of the present invention in the direction facing the second plane, only the third component angle γ of fourth composite angle δ is visible in FIG. 2.

The third straight section 230 of the third distal end section 170 of the cannula needle 100 terminates with a closed blunt tip 140 and has an exterior surface 270, which is a portion of the exterior surface 115 of the tubular sidewall 110 of the cannula needle 100. In addition, the third straight section 230 has a plurality of apertures 260 that pass through the sidewall 110 of the cannula needle 100 and extend to a section 280 of the exterior surface 270 of the third straight section 230. The section 280 of the exterior surface 270 at least substantially faces the second central axis 210, permitting the source of fluid to be capable of being in fluid communication with an area 290 external to the third straight section 230 adjacent to the plurality of apertures 260.

The angulation of the first central axis 190, second central axis 210, and third central axis 240 permit the third straight section 230 to be moved around and along a vein in a spiral, or corkscrew, motion since the first central axis 190 is only co-planar with the second central axis 210 and is not co-planar with the third central axis 240. This permits the second straight section 200 to remain positioned along the length of the vein while allowing the third straight section 230 to be rotated around the vein and moved along the vein. A fluid, such as tumescent anesthesia can thus be evenly applied to the surface of a vein by adjusting and rotating the first straight section 180 of the cannula needle 100, which remains outside of the limb, while the third straight section 230 is completely within the tissue of the limb containing the vein to be treated. The present invention is envisioned to be used to apply tumescent anesthesia to veins of various lengths. A cannula needle 100 with a second straight section 200 that is about 60.0 cm in length can treat a longer vein than a cannula needle 100 with a shorter second straight section 200 that is about 10.0 cm in length, which would be used to treat a much shorter vein.

Figure 3:
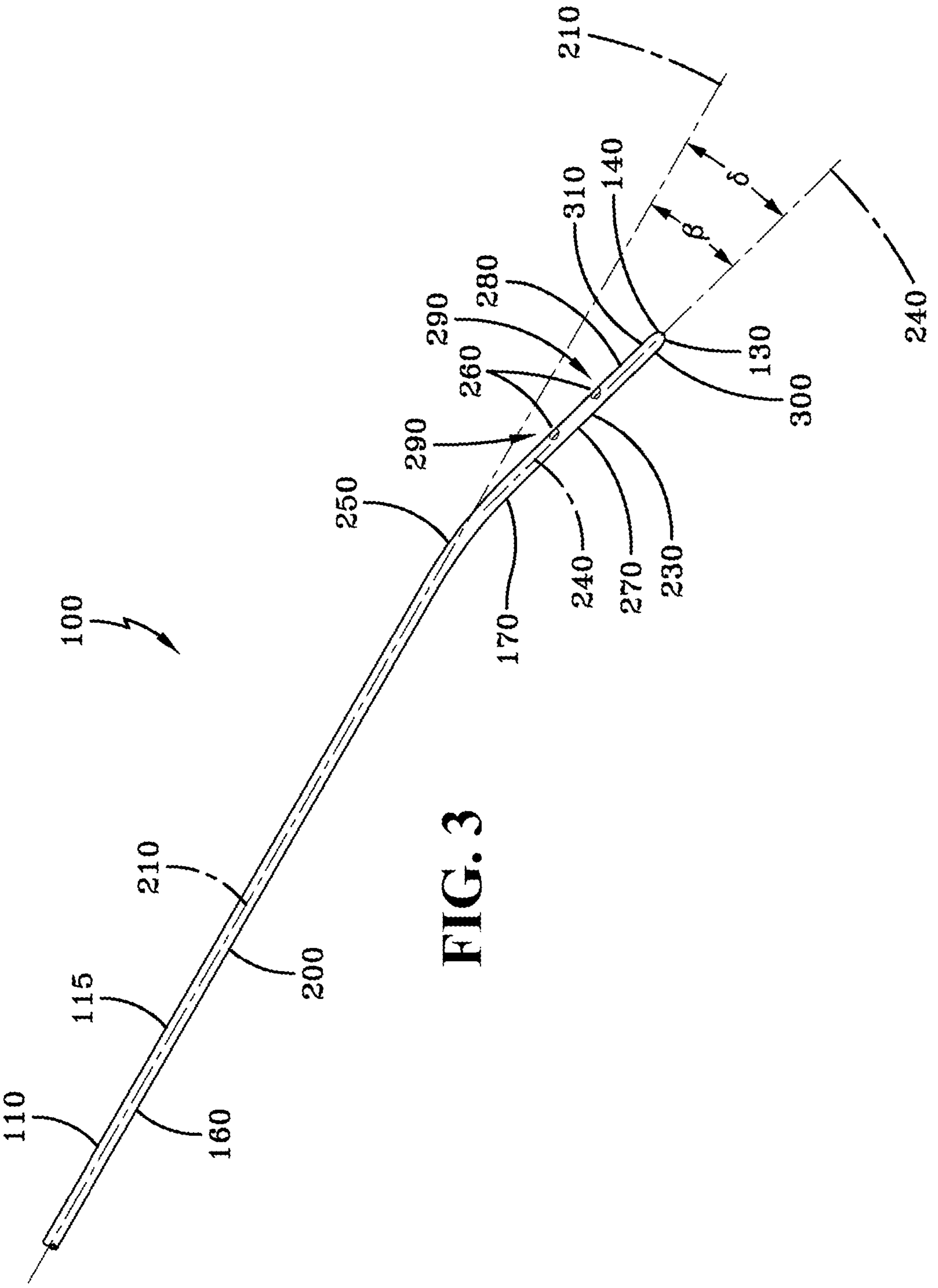
FIG. 3 is a side view of a portion of the cannula needle shown in FIG. 1.
Figure 4:
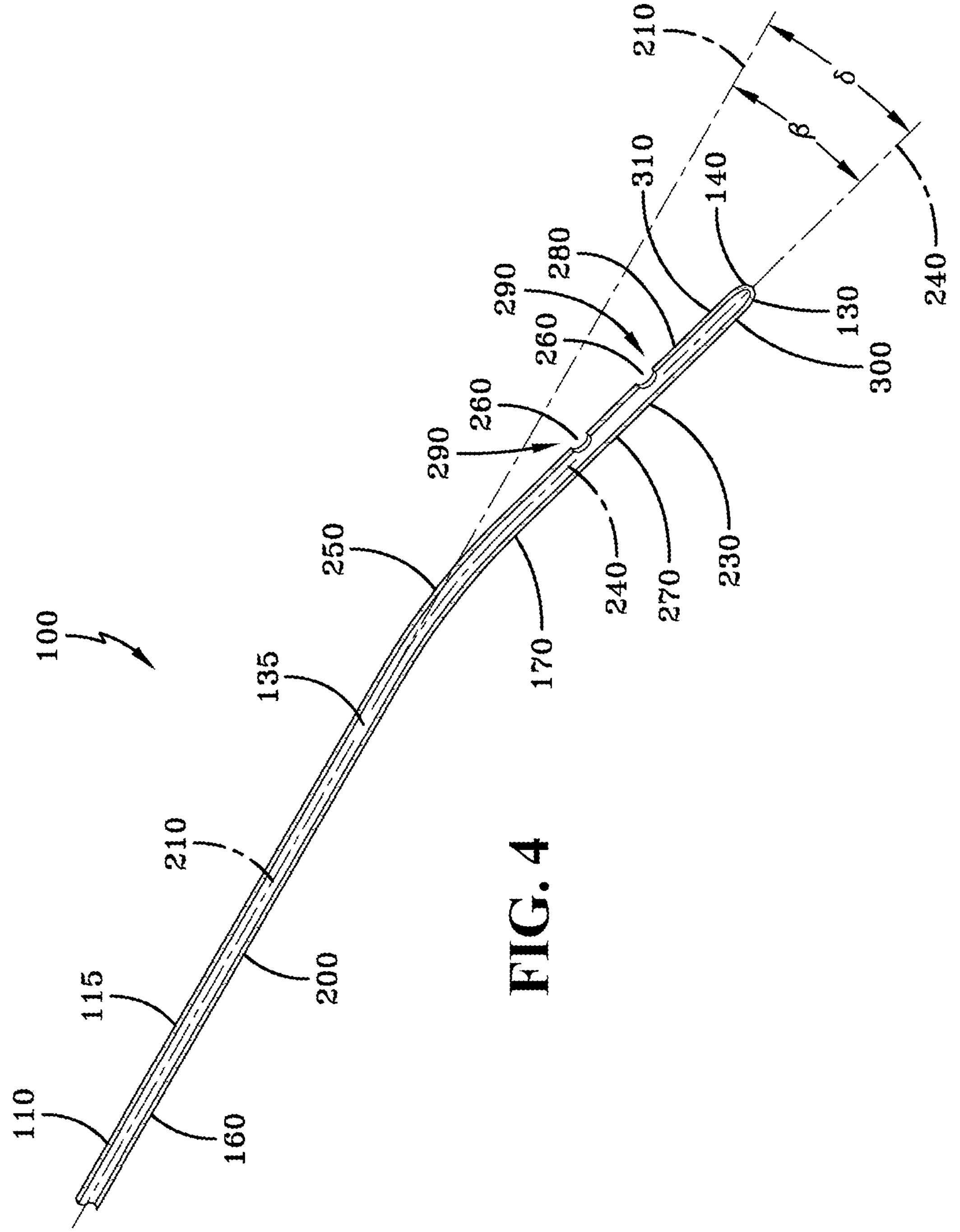
FIG. 4 is a cross-section of the portion of the cannula needle shown in FIG. 3.

FIG. 3, which is a side view of a portion of the cannula needle 100 of FIG. 1, and FIG. 4 which is a cross section of the portion of the cannula needle 100 shown in FIG. 3, include only a portion of the second main body section 160 and the third distal end section 170 in order to show the hollow central lumen 135 and the position of the plurality of apertures 260 more clearly. As the source of tumescent anesthesia is in fluid communication with the area 290 external to the third straight section 230 adjacent to the plurality of apertures 260, the application of the tumescent anesthesia to the surface of the vein can be controlled by the surgeon as the tumescent anesthesia is only flowing to the area 290 adjacent to the plurality of apertures 260. As the plurality of apertures 260 at least substantially face the second central axis 210, the general direction of the flow of the tumescent anesthesia will be apparent to the surgeon during the application of the tumescent anesthesia. By positioning the plurality of apertures 260 so that they at least substantially face the second central axis 210, moving the third straight section 230 around the vein by rotating the second straight section 200 around its axis 210 permits the surgeon using the cannula needle 100 to have the ability to consistently have the plurality of apertures 260 face away from the general direction of the vein to be treated. This enables the dissection of nerves and other important structures away from the vein using fluid pressure, while further reducing the risk of tumescent anesthesia entering the internal vein lumen. The angulation of the third central axis 240 away from the second central axis 210 at fourth composite angle δ, as set forth herein, permits the surgeon to readily rotate the plurality of apertures 260 in a circular or spiral pattern in the range of about 1.0 cm to about 2.0 cm around the outer wall of the vein to be treated. The shape of the apertures 260 may be in any appropriate shape as known in the art, such as circular or oval, or any similar functional shape. Infiltration of a fluid, such as tumescent anesthesia, into and through the cannula needle 100, through the plurality of apertures 260, and into the patient, may be accomplished by any method used in art, such an infiltration pump, hand pump, or any other similar method as known in the art. Alternatively, the force of gravity may be used to force the fluid into and through the cannula needle 100, through the plurality of apertures 260, and into the patient.

In a preferred embodiment of the cannula needle 100 of the present invention, no apertures 260 are present within a distal end region 300 of the third straight section 230, which is the region 300 of the third straight section 230 located within about 0.2 cm of the closed blunt tip 140. This is so that if the closed blunt tip 140 accidentally perforates a vein wall, no bolus of tumescent anesthesia would be accidentally injected into such a vein. As the closed blunt tip 140 is closed, rather than open, if the closed blunt tip 140 perforates a vein, the closed blunt tip 140 would have to travel at least a couple of millimeters into a vein before one of the plurality of apertures 260 would physically enter the lumen of the vein, significantly reducing the risk of causing an intravenous injection of a bolus of tumescent anesthesia. Each aperture 260 is preferably positioned at least about 0.2 cm away from the other apertures 260 in order to maintain the structural integrity of the third straight section 230 of the cannula needle 100.

In a preferred embodiment of the cannula needle 100 of the present invention, when the length of the third straight section 230 is in the range of about 1.0 cm to about 3.0 cm, only two apertures 260 are present to permit the surgeon to have more control over the application of the tumescent anesthesia. In a more preferred embodiment, the apertures 260 begin about 0.5 cm from the closed blunt tip 140 and are spaced about 0.5 cm apart from each other.

In an alternate preferred embodiment of the cannula needle 100 of the present invention, when the length of the third straight section 230 is in the range of about 4.0 to about 6.0 cm, only four apertures 260 are present to permit the surgeon to have more control over the application of the tumescent anesthesia. In a more preferred alternate embodiment, the four apertures 260 begin about 0.5 cm from the closed blunt tip 140 and are spaced about 0.5 cm apart from each other.

In using the cannula needle 100 of the present invention, ultrasound guidance may be used to position the third straight section 230 along the length of the vein to be treated with tumescent anesthesia while the third straight section 230 is present in the limb containing the vein. In an embodiment of the present invention, an echogenicity portion 310 of at least a portion of the exterior surface 270 of the third straight section 230 is provided to increase ultrasound clarity relative to the rest of the exterior surface 115 of the tubular sidewall 110. Such an increase in echogenicity may be accomplished by increasing the roughness of at least a portion of the exterior surface 270. Echogenicity is the ability to bounce an echo, e.g. return the signal in medical ultrasound examinations. Such roughening may be accomplished by scratching or chemically etching at least a portion 310 of the exterior surface 270 as is known in the art. An echogenicity portion 310 may include a porous material, such as a porous metal or plastic, and the porosity may improve echogenicity. In addition, the echogenicity portion may include a different material than the rest of the exterior surface 115 of the tubular sidewall 110, such as a metallic coating, that may be a porous coating to increase echogenicity. In a more preferred embodiment, at least a portion 310 of the exterior surface 270 of the third straight section 230 has a greater echogenicity than the rest of the exterior surface 115 of the tubular sidewall 110, where the portion 310 of the exterior surface 270 is located between the plurality of apertures 260 and the distal end 130 of the tubular cannula needle 100.

Given the length of the cannula needle 100 of the present invention, the cannula needle 100 is preferably composed of metal for the purpose of stability. In a preferred embodiment, the cannula needle 100 of the present invention is composed of surgical stainless steel. In a preferred embodiment, the diameter of at least a portion of the cannula needle 100 including the second straight section 200 and the third straight section 230 is in the range of about 0.15 to about 0.35 cm. In a more preferred embodiment, the diameter of at least a portion of the cannula needle 100 including the second straight section 200 and the third straight section 230 is about 0.20 cm. The diameter of the first straight section 180 may be the same as the diameter of the second straight section 200 and the third straight section 230, or at least a portion of the diameter of the first straight section 180 may be slightly larger, depending on any additional surgical instrumentation used to ultimately connect the cannula needle 100 with a source of fluid, as is known in the art.

Figure 5:
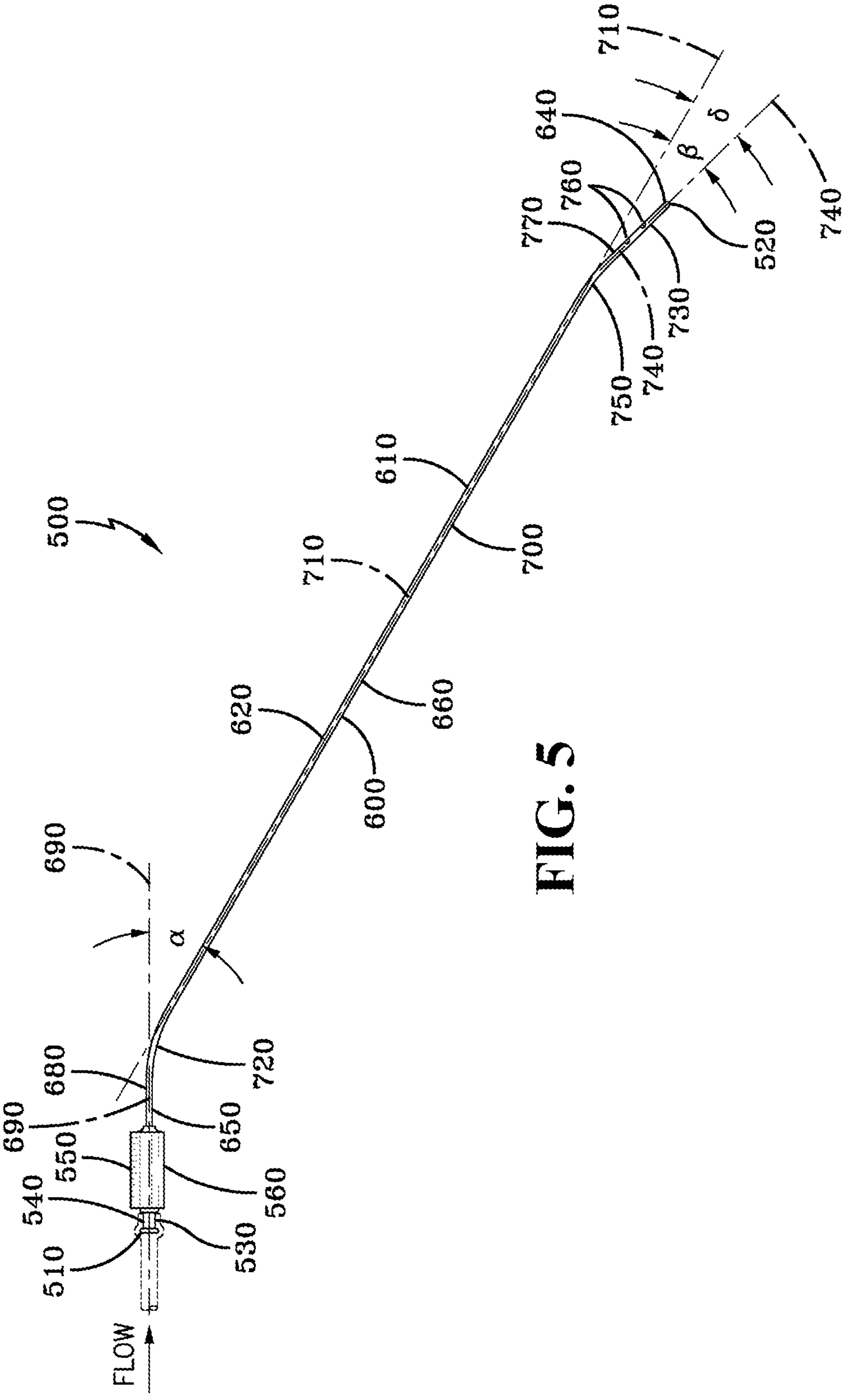
FIG. 5 is a side view of a surgical cannula of the present invention.
Figure 8:
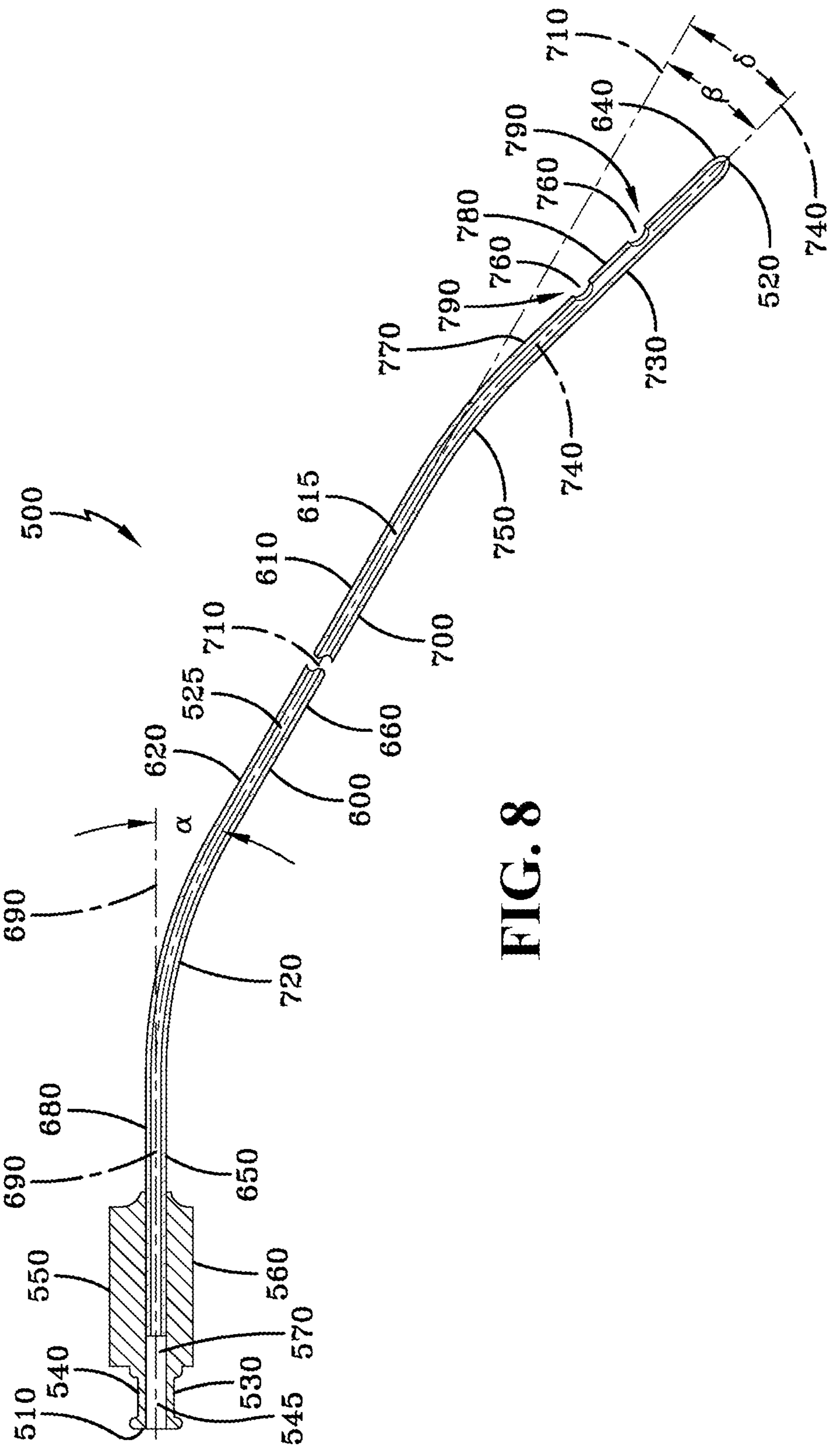
FIG. 8 is a sectioned cross-section of the surgical cannula shown in FIG. 5.

As further set forth herein, the side view of FIG. 5 of an embodiment of the surgical cannula of the present invention is a view facing the first reference plane, such that the angulation of elements in the first reference plane is shown. The top view of FIG. 6, which the embodiment of the surgical cannula of the present invention shown in FIG. 5, is a view facing the second reference plane, such that the angulation of elements in the second reference plane is shown. FIG. 8 is a sectioned cross-section of a portion of the surgical cannula shown in FIG. 5.

Figure 6:
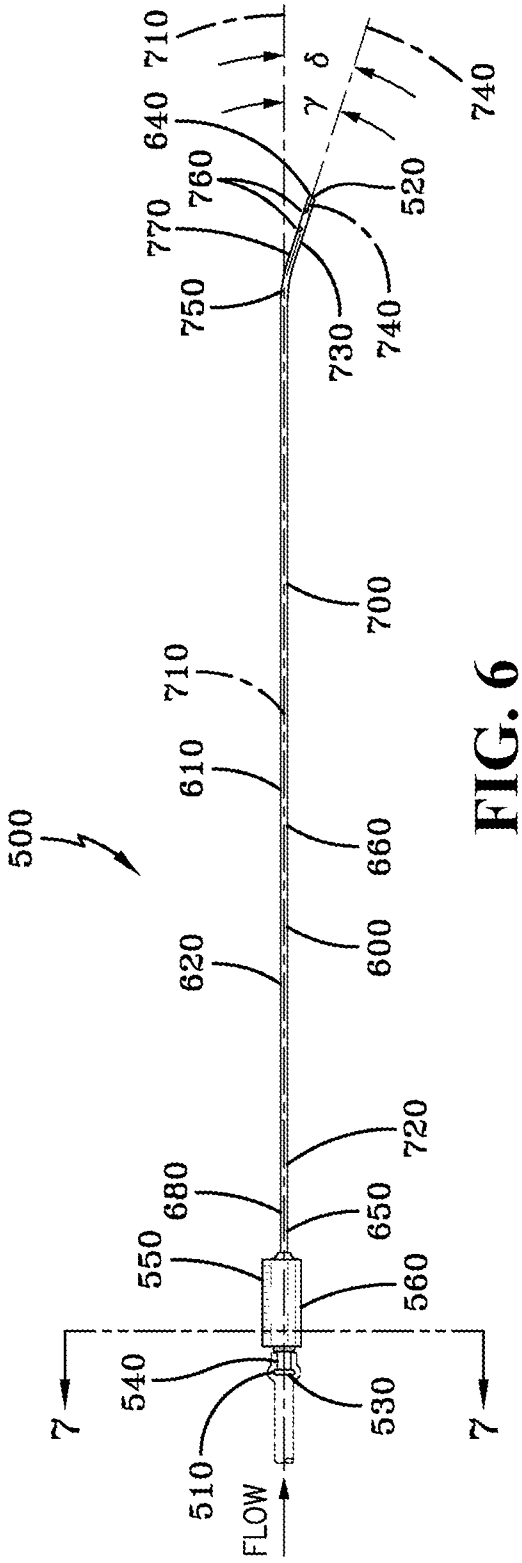
FIG. 6 is a top view of the surgical cannula shown in FIG. 5.

As shown in FIG. 5, FIG. 6, and FIG. 8, the present invention is also a surgical cannula 500 comprising two ends, a proximal end 510 and a distal end 520. The surgical cannula 500 further comprises a hollow fluid connector 530 that extends from the proximal end 510 and allows attachment of the surgical cannula 500 to a source of fluid. As is known in the art one such fluid is tumescent anesthesia, which may be provided by IV line or other source of tumescent anesthesia as known in the art. The fluid connector 530 comprises a first side wall 540. The surgical cannula 500 further comprises a handle 550 that extends from the fluid connector 530. The handle 550 comprises a second side wall 560. The surgical cannula 500 further comprises a tubular needle 600 that extends from the handle 550 to a closed blunt tip 640 at the distal end 520. The tubular needle 600 comprises a third tubular side wall 610 that comprises the body of the tubular needle 600.

The surgical cannula 500 further comprises a hollow central lumen 525 that is defined by the first side wall 540 of the fluid connector 530, by the second side wall 560 of the handle 550, and by the third tubular side wall 610 of the tubular needle 600. The first side wall 540 of the fluid connector 530 defines a first portion 545 of the hollow central lumen 525. The second side wall 560 of the handle 550 defines a second portion 570 of the hollow central lumen 525. The third side wall 610 of the tubular needle 600 defines a third portion 615 of the hollow central lumen 525. The hollow central lumen 525 extends the entire length of the surgical cannula 500 from the fluid connector 530 to the closed blunt tip 640. The hollow central lumen 525 is capable of being in fluid communication with the source of fluid.

Figure 7:
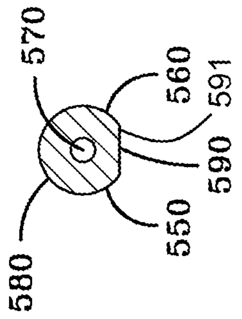
FIG. 7 is a cross-section of the handle of the surgical cannula shown in FIG. 5.

The handle 550 of the surgical cannula 500 permits the surgeon to readily hold, move and rotate the surgical cannula 500 and the tubular needle 600 during the process of infiltration of the tumescent anesthesia into the area between the fascia, or other tissue, such as, but not limited to skin and nerves, and the wall of the varicose vein to be ablated. As shown in FIG. 7, which is a cross-section view of the handle 550, a first portion 580 of the exterior surface of the second sidewall 560 of the handle 550 is substantially cylindrical in shape while a second portion 590 of the exterior surface of the second sidewall 560 has an orientation feature 591 such as protrusion from the exterior surface, or wherein the second portion is flat, which assists the surgeon in ascertaining the orientation of the tubular needle 600 within the patient during surgery given the multi-axial orientation of the tubular needle 600. The second portion 570 of the hollow central lumen 525 defined by the second side wall 560 of the handle 550 is also visible in FIG. 7. Other configurations for the handle 550 that allow the surgeon to ascertain the orientation of tubular needle 600 are also contemplated within the scope of the present invention such as, but not limited to, small nodes on the surface of the handle, a rougher area on the handle, a small raised textured section on the handle, or any other configuration as known in the art.

The third tubular side wall 610 that comprises the body of the tubular needle 600 further comprises an exterior surface 620. The third tubular side wall 610 has three main sections, a first proximal end section 650, a second main body section 660, and a third distal end section 670.

The first proximal end section 650 of the tubular needle 600 has a first straight section 680. The first straight section 680, being tubular, has a first central axis 690. The length of the first straight section 680 is in the range of about 0.5 cm to about 5.5 cm. In a more preferred embodiment, the length of the first straight section 680 is in the range of about 1.0 cm to about 4.0 cm. In a more preferred embodiment, the length of the first straight section 680 is about 2.0 cm. In an alternate embodiment, the length of the first straight section 680 is about 3.5 cm. In another alternate embodiment, the length of the first straight section 680 is about 1.0 cm.

The second main body section 660 of the tubular needle 600 extends from the first proximal end section 650 and has a second straight section 700. The second straight section 700, being tubular, has a second central axis 710. In order to show more detail in FIG. 8, the second straight section 700 is sectioned so that a portion of the length of the second straight section 700 is not shown. There is no break in the second straight section 700 in FIG. 8, rather the sectioning is for illustrative purposes only. The length of the second straight section 700 is preferably in the range of about 10.0 cm to about 60.0 cm. In one embodiment of the present invention, the length of the second straight section 700 is about 10.0 cm. In another embodiment of the present invention, the length of the second straight section 700 is about 20.0 cm. In another embodiment of the present invention, the length of the second straight section 700 is about 30.0 cm. In another embodiment of the present invention, the length of the second straight section 700 is about 40.0 cm. In another embodiment of the present invention, the length of the second straight section 700 is about 45.0 cm. In another embodiment of the present invention, the length of the second straight section 700 is about 50.0 cm. In another embodiment of the present invention, the length of the second straight section 700 is about 60.0 cm.

In a preferred embodiment, the first proximal end section 650 of the tubular needle 600 further comprises a first curved transitional section 720 extending from the first straight section 680, with the second straight section 700 extending from first curved transitional section 720. Such curvature prevents the use of sharp corners to prevent damage to the tissue of the limb into which the tubular needle 600 is inserted. In a more preferred embodiment, the first curved transitional section 720 has a length in the range of about 0.4 cm to about 2.0 cm. In an even more preferred embodiment, the first curved transitional section 720 has a length of about 1.2 cm.

The surgical cannula 500 of the present invention is intended to permit the insertion of the tubular needle 600 through the skin of a limb of a person to permit the injection of tumescent anesthesia in the tissue around a vein. In the present invention, the second central axis 710 is angled away from the first central axis 690 at a preselected angle $\alpha$ in a first reference plane, such that the first central axis 690 and the second central axis 710 are coplanar in the first plane. The angle $\alpha$ is in the range of about 35° to about 45°. In a more preferred embodiment, the angle $\alpha$ is about 40°. Having the second central axis 710 angled away from the first central axis 690 at angle $\alpha$ permits a surgeon to readily adjust the position of the tubular needle 600 by manipulating the handle 550 of the surgical cannula 500. Due to human anatomy, using the cannula 500 to inject tumescent anesthesia around a vein of any significant length requires that the third straight section 730 of the cannula needle 600 and at least a portion of the second straight section 700 of the tubular needle 600 be inserted under the skin of the limb through a small hole in the skin of the limb. As the handle 550 of the surgical cannula 500 is intended to be used to manipulate the position of the tubular needle 600 within the limb, the handle 550 must remain outside of the limb to be readily repositioned by the surgeon. The angulation of the second central axis 710 with respect to the first central axis 690 permits the ready adjustment both the second straight section 700 and third straight section 730 during surgery. The geometry of the surgical cannula 500 of the present invention therefore allows the handle 550 of the surgical cannula 500 to remain positioned away from the skin of the limb during surgical procedures.

The third distal end section 670 of the tubular needle 600 has a third straight section 730. The third straight section 730, being tubular, has a third central axis 740. In one embodiment of the present invention, the length of the third straight section 730 is in the range of about 1.0 cm to about 3.0 cm. In a more preferred embodiment of the present invention, the length of the third straight section 730 is about 2.0 cm.

In a preferred embodiment, the second main body section 660 of the tubular needle 600 further comprises a second curved transitional section 750 extending from the second straight section 700, with the third straight section 730 extending from the second curved transitional section 750. Such curvature prevents the use of sharp corners to prevent damage to the tissue of the limb into which the cannula needle 100 is inserted. In a more preferred embodiment, the second curved transitional section 750 has a length in the range of about 0.4 cm to about 1.2 cm. In an even more preferred embodiment, the second curved transitional section 750 has a length of about 0.8 cm.

As set forth herein, the line of intersection of the first reference plane and a second reference plane is congruent with the second central axis 710 of the tubular needle 600. The third central axis 740 is angled away from the second central axis 710 at a fourth composite angle $\delta$, the fourth composite angle $\delta$ being a combination of a second preselected component angle $\beta$ in the first plane and a third preselected component angle $\gamma$ in the second plane. From a geometric standpoint, since the first plane and the second plane are perpendicular, the fourth composite angle $\delta$ is characterized as having two perpendicular angular components, angle $\beta$ and angle $\delta$. Thus, the geometric configuration of the first central axis 690, the second central axis 710, and the third central axis 740 of the tubular needle 600 of the present invention requires that the first central axis 690 not be coplanar with the third central axis 740.

In an embodiment of the present invention, when the third straight section 730 of the tubular needle 600 is in the range of about 1.0 cm to about 3.0 cm, the fourth composite angle δ is in the range of about 20.8° to about 40.0°, with the second component angle β being in the range of about 15° to about 35°, and with the third component angle γ being in the range of about 15° to about 25°. In a more preferred embodiment, the fourth composite angle δ is about 30.6°, with the second component angle β being about 25° and the third component angle γ being about 20°.

In an alternate embodiment of the present invention, the third straight section 730 of the tubular needle 600 has a length in the range of about 4.0 cm to about 6.0 cm. In this alternate embodiment, the fourth composite angle δ is in the range of about 7.1° to about 20.8°, with the second component angle β being in the range of about 5° to about 15° and the third component angle γ being in the range of about 5° to about 15°. In a more preferred alternate embodiment, the fourth composite angle δ is about 14.0°, with the second component angle β being about 10° and the third component angle γ being about 10°.

As FIG. 5 and FIG. 8 are views of the surgical cannula 600 of the present invention in the direction facing the first plane, only the second component angle β of fourth composite angle δ is visible in FIG. 5 and FIG. 8. Likewise, as FIG. 6 is a view of the surgical cannula 600 of the present invention in the direction facing the second plane, only the third component angle γ of fourth composite angle δ is visible in FIG. 6.

The third straight section 730 of the third distal end section 670 of the tubular needle 600 terminates with the closed blunt tip 640 and has an exterior surface 770, which is a portion of the exterior surface 620 of the sidewall 610 of the tubular needle 600. In addition, the third straight section 730 has a plurality of apertures 760 that pass through the sidewall 610 of the tubular needle 600 and extend to a section 780 of the exterior surface 770 of the third straight section 730. The section 780 of the exterior surface 770 at least substantially faces the second central axis 710, permitting the source of fluid to be capable of being in fluid communication with an area 790 external to the third straight section 730 adjacent to the plurality of apertures 760.

The angulation of the first central axis 690, second central axis 710, and third central axis 740 permits the third straight section 730 to be moved around and along a vein in a spiral, or corkscrew, motion since the first central axis 690 is only co-planar with the second central axis 710 and is not co-planar with the third central axis 740. This permits the second straight section 700 to remain positioned along the length of the vein while allowing the third straight section 730 to be rotated around the vein and moved along the vein. A fluid, such as tumescent anesthesia can thus be evenly applied to the surface of a vein by adjusting and rotating the handle 550, which remains outside of the limb, while the third straight section 730 is completely within the tissue of the limb containing the vein to be treated. The present invention is envisioned to be used to apply tumescent anesthesia to veins of various lengths. A surgical cannula 500 having a tubular needle 600 with a second straight section 700 that is about 60.0 cm in length can treat a longer vein than a surgical cannula 500 having a tubular needle 600 with a shorter second straight section 700 that is about 10.0 cm in length, which would be used to treat a much shorter vein.

Figure 9:
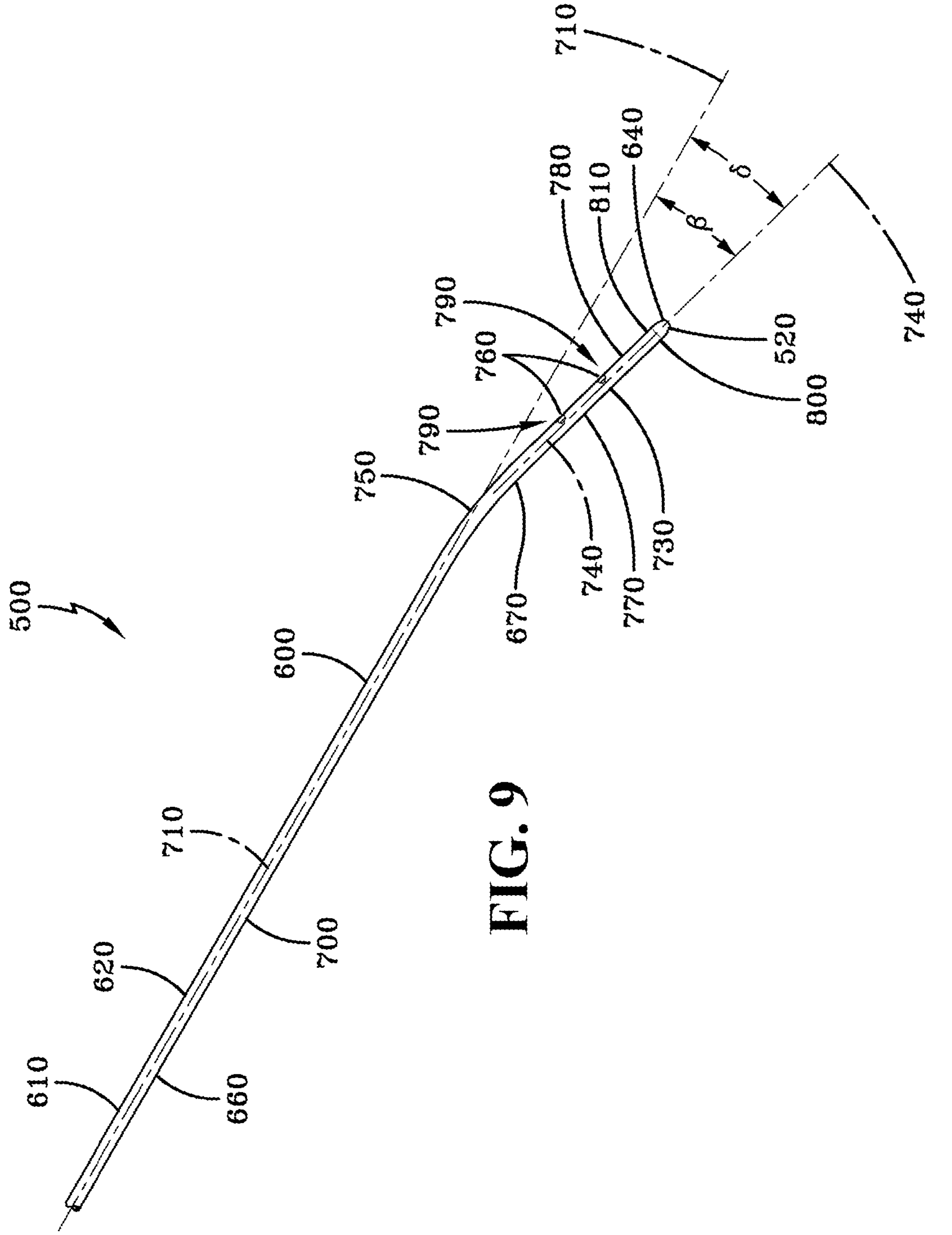
FIG. 9 is a side view of a portion of the surgical cannula shown in FIG. 5.
Figure 10:
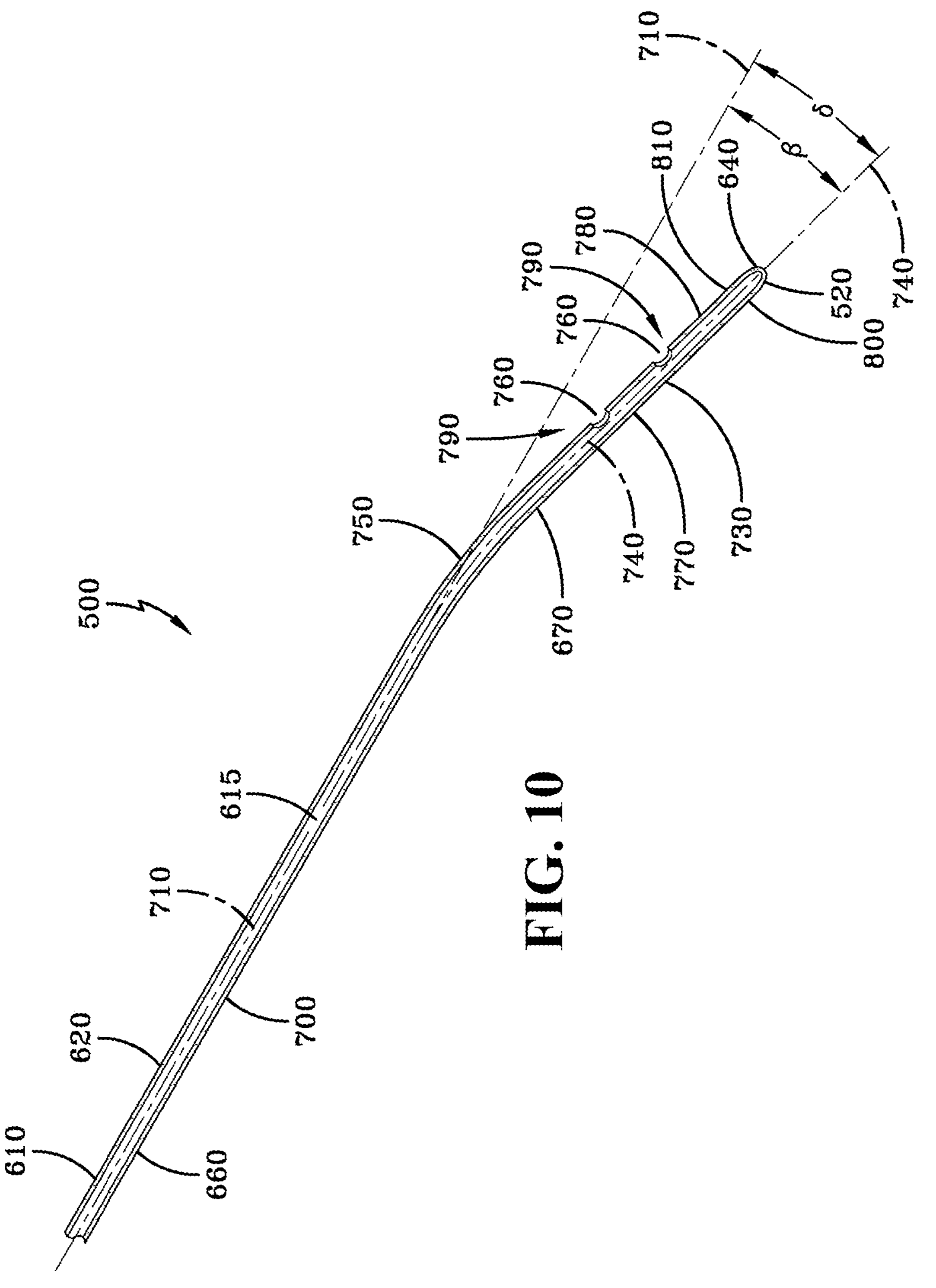
FIG. 10 is a cross-section of the portion of the surgical cannula shown in FIG. 9.
Figure 11:
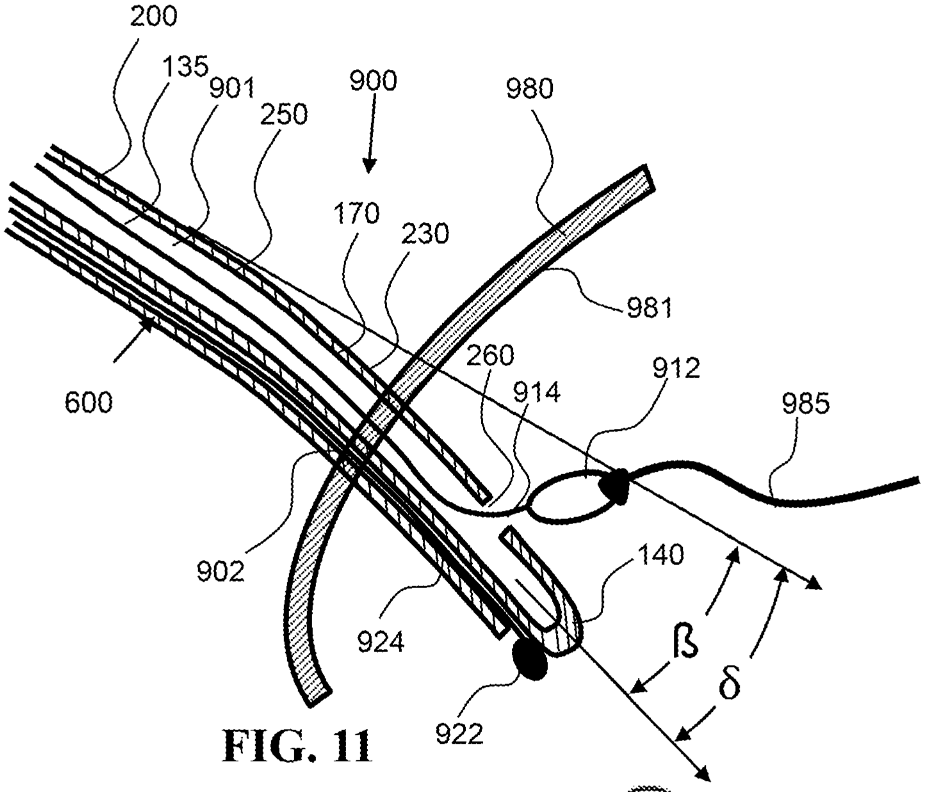
FIG. 11 shows a cross-sectional view of the distal end of a tubular needle having two lumens, a first lumen having a snare tether extending therethrough and coupled with a snare and a second lumen having a light device and light tether extending therein.
Figure 12:
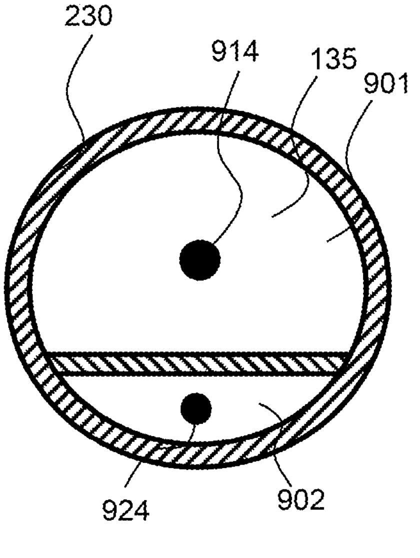
FIG. 12 shows a cross-sectional view along line 12-12 of FIG. 11.

FIG. 9, which is a side view of a portion of the surgical cannula 500 shown in FIG. 5, and FIG. 10, which is a cross-section of the portion of the tubular needle 500 shown in FIG. 9, include only a portion of the second main body section 660 and the third distal end section 670 of the tubular needle 600 in order to show the third portion 615 of the hollow central lumen 525 and the positioning of the plurality of apertures 760 more clearly. As the source of tumescent anesthesia is in fluid communication with the area 790 external to the third straight section 730 adjacent to the plurality of apertures 760, the application of the tumescent anesthesia to the surface of the vein can be controlled by the surgeon as the tumescent anesthesia is only flowing to the area 790 adjacent to the plurality of apertures 760. As the plurality of apertures 760 at least substantially face the second central axis 710, the general direction of the flow of the tumescent anesthesia will be apparent to the surgeon during the application of the tumescent anesthesia. By positioning the plurality of apertures 760 so that they at least substantially face the second central axis 710, moving the third straight section 730 around the vein by rotating the second straight section 700 around its axis 710 permits the surgeon using the surgical cannula 500 to have the ability to consistently have the plurality of apertures 760 face away from the general direction of the vein to be treated. This enables the dissection of nerves and other important structures away from the vein using fluid pressure, while further reducing the risk of tumescent anesthesia entering the internal vein lumen. The angulation of the third central axis 740 away from the second central axis 710 at fourth composite angle δ, as set forth herein, permits the surgeon to readily rotate the plurality of apertures 760 in a circular or spiral pattern in the range of about 1.0 cm to about 2.0 cm around the outer wall of the vein to be treated. The shape of the apertures 760 may be in any appropriate shape as known in the art, such as circular or oval, or any similar functional shape. Infiltration of a fluid, such as tumescent anesthesia, into and through the surgical cannula 500, through the plurality of apertures 760, and into the patient, may be accomplished by any method used in art, such an infiltration pump, hand pump, or any other similar method as known in the art. Alternatively, the force of gravity may be used to force the fluid into and through the surgical cannula 500, through the plurality of apertures 760, and into the patient.

In a preferred embodiment of the surgical cannula 500 of the present invention, no apertures 760 are present within a distal end region 800 of the third straight section 730 of the tubular needle 600, which is the region 800 of the third straight section 730 located within about 0.2 cm of the closed blunt tip 640. This is so that if the closed blunt tip 640 accidentally perforates a vein wall, no bolus of tumescent anesthesia would be accidentally injected into such a vein. As the closed blunt tip 640 is both closed, rather than open, if the closed blunt tip 640 perforates a vein, the closed blunt tip 640 would have to travel at least a couple of millimeters into a vein before one of the plurality of apertures 760 would physically enter the lumen of the vein, significantly reducing the risk of causing an intravenous injection of a bolus of tumescent anesthesia. Each aperture 760 is preferably positioned at least about 0.2 cm away from the other apertures 760 in order to maintain the structural integrity of the third straight section 730 of the tubular needle 600.

In a preferred embodiment of the surgical cannula 600 of the present invention, when the length of the third straight section 730 of the tubular needle 600 is in the range of about 1.0 cm to about 3.0 cm, only two apertures 760 are present to permit the surgeon to have more control over the application of the tumescent anesthesia. In a more preferred embodiment, the apertures 760 begin about 0.5 cm from the closed blunt tip 640 and are spaced about 0.5 cm apart from each other.

In an alternate preferred embodiment of the surgical cannula 600 of the present invention, when the length of the third straight section 730 of the tubular needle 600 is in the range of about 4.0 to about 6.0 cm, only four apertures 760 are present to permit the surgeon to have more control over the application of the tumescent anesthesia. In a more preferred alternate embodiment, the four apertures 760 begin about 0.5 cm from the closed blunt tip 640 and are spaced about 0.5 cm apart from each other.

In using the surgical cannula 500 of the present invention, ultrasound guidance may be used to position the third straight section 730 of the tubular needle 600 along the length of the vein to be treated with tumescent anesthesia while the third straight section 730 is present in the limb containing the vein. In an embodiment of the present invention, an echogenicity portion 810 of at least a portion of the exterior surface 770 of the third straight section 730 is provided to increase echogenicity relative to the rest of the exterior surface 620 of the third sidewall 610 of the tubular needle 600. Such an increase in echogenicity may be accomplished by increasing the roughness of at least a portion 810 of the exterior surface 770 of the third straight section 730. Such roughening may be accomplished by scratching or chemically etching at least a portion 810 of the exterior surface 770 of the third straight section 730 as is known in the art. In a more preferred embodiment, at least a portion 810 of the exterior surface 770 of the third straight section 730 has a greater echogenicity than the rest of the exterior surface 620 of the third sidewall 610 of the tubular needle 600, where the portion 810 of the exterior surface 770 is located between the plurality of apertures 760 and the distal end of the tubular needle 600.

Given the length of the surgical cannula 500 of the present invention, the surgical cannula 500 is preferably composed of metal for the purpose of stability. In a preferred embodiment, the surgical cannula 500 of the present invention is composed of surgical stainless steel. In a preferred embodiment, the diameter of at least a portion of the tubular needle 600 including the second straight section 700 and the third straight section 730 is in the range of about 0.15 to about 0.35 cm. In a more preferred embodiment, the diameter of a least a portion of the tubular needle 600 including the second straight section 700 and the third straight section 730 is about 0.20 cm. The diameter of the first straight section 680 may be the same as the diameter of the first straight section 680 and the second straight section 700, or at least a portion of the diameter of the first straight section 680 may be slightly larger, depending on how the first straight section 680 is connected to the handle 550 as is known in the art.

Referring now to FIGS. 11 to 14, a tubular needle 600 as described herein, may be a ventriculoperitoneal shunt tubular needle 900 for use in ventriculoperitoneal shunt procedures. When the pressure of cerebral spinal fluid in the brain is high neurosurgeons may place a shunt in the brain tunnel through the subcutaneous tissue all the way down from the base of the skull and neck to below the diaphragm and connect to the peritoneal cavity so that the fluid drains from the brain into the abdomen. The tubular needle, as described herein, may be used for creating a pathway and locating the shunt from said base of the skull to the abdomen. The tubular needle for this procedure may include two lumens, a first lumen 901, a hollow central lumen 135 as described herein, to pass a snare tether 914, such as a stiff suture, or guide wire, which extends to a snare 912 to couple with a shunt tether, such as a suture or guide wire, to be eventually coupled with the shunt and pulled into the peritoneal cavity, and a second lumen 902 for light device 922, such as a fiberoptic light coupled to a light tether 924, to indicate where the distal end of the tubular needle is located, as described.

Figure 13:
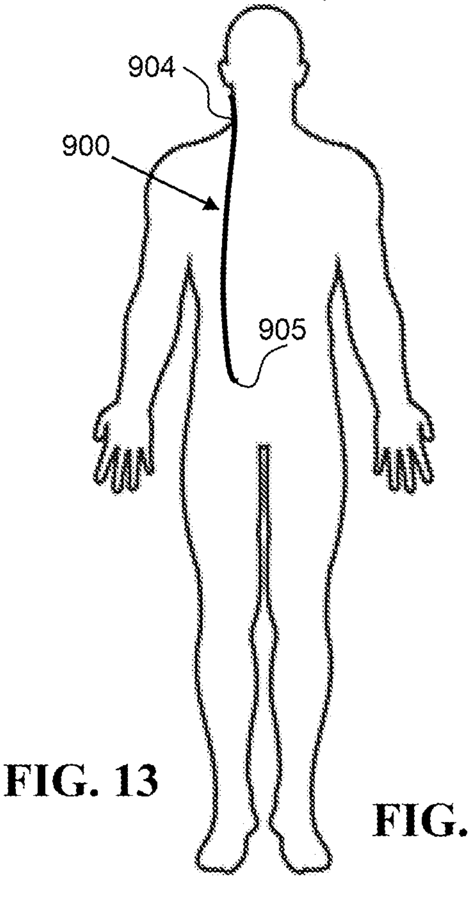
FIG. 13 shows a front view of a person and a ventriculoperitoneal shunt tubular needle extending from the neck to the abdomen of the person.
Figure 14:
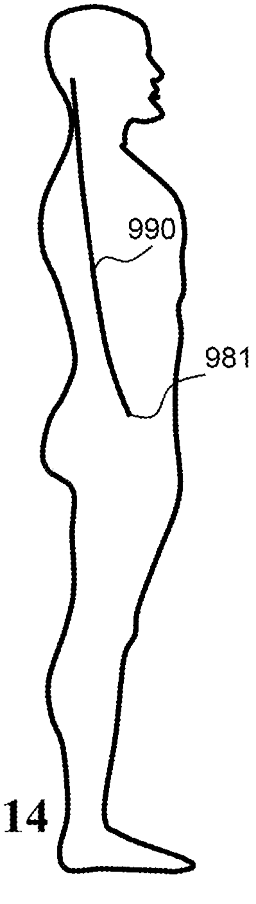
FIG. 14 shows a side view of a person and a ventriculoperitoneal shunt extending from the neck to the abdomen of the person.

The steps of a ventriculoperitoneal shunt procedures are as follows: Insert the blunt tip 140 of the ventriculoperitoneal shunt tubular needle 900 into a person's body, proximal to the neck and the move the blunt tip 140 from neck all the way down to below the diaphragm below the rib cage. The light device provides light for observation of the pathway through the subcutaneous tissue until the blunt tip approaches the peritoneal cavity. At this stage the tubular needle may be turned to direct the blunt tip toward the peritoneal cavity. A laparoscope can detect the light from the light device 922, such as a fiberoptic light device, through the peritoneal cavity 981 and once the location of the blunt tip 140 is confirmed a small perforation is made in the peritoneal wall 980 laparoscopically. The snare tether 914, such as a stiff suture or guide wire is then passed into the peritoneal cavity and the snare 912 is coupled with a shunt snare 985, such as a guide wire or suture. The tubular needle 600 can then be withdrawn pulling the shunt snare 985 from the peritoneal cavity 981 to the neck. The shunt tether 985 can then be coupled with the ventriculoperitoneal shunt 990 and the ventriculoperitoneal shunt can be pulled from the neck down into the peritoneal cavity 981, as shown in FIG. 14. The ventriculoperitoneal shunt 990 may be tied to or otherwise attached to the snare tether 985 and the snare tether can be pulled into the peritoneal cavity and placed in its appropriate position. This procedure has the advantage of safety and the reduced risk of injuring the lung or causing pneumothorax while placing the catheter. Also, the entire procedure can be performed laparoscopically. As shown in FIG. 13, the ventriculoperitoneal shunt tubular needle 900 extends from a proximal end 904, to a distal end 905 in the abdomen or peritoneal cavity.

It will be apparent to those skilled in the art that various modifications, combinations, and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A tubular needle of a surgical cannula, the tubular needle comprising:

a proximal end, the proximal end being open and capable of being in fluid communication with a source of fluid;

a distal end, the distal end comprising a closed blunt tip;

a tubular side wall defining a hollow central lumen, a first proximal end section, the first proximal end section comprising:

a first straight section extending from the proximal end and having a first central axis; and a second main body section extending from the first proximal end section, the second main body section comprising:

a second straight section having a length in a range of 10.0 cm to 60.0 cm, the second straight section further having a second central axis, the second central axis being angled away from the first central axis at a first angle in a first plane, such that the first central axis and the second central axis are coplanar in the first plane, the first angle being less than 90°;

a third distal end section extending from the second main body section to the closed blunt tip, the third distal end section comprising:

a third straight section having a third central axis, the third central axis being angled away from the second central axis at a fourth composite angle, the fourth composite angle being a combination of a second angle and a third angle, such that the third central axis is effectively angled away from the second central axis both at the second angle in the first plane and at the third angle in a second plane, the second plane being perpendicular to the first plane such that the second central axis is located on a line of intersection of the first plane and the second plane, the second angle being less than 90° and the third angle being less than 90°, such that the third central axis is not coplanar with the first central axis; and an aperture through the tubular side wall of the third straight section and configured through the tubular side wall to face the second central axis, wherein the hollow central lumen extends from the proximal end to the aperture, the hollow central lumen being capable of being in fluid communication with the source of fluid; and wherein the length of the second straight section is more than twice a length of the first straight section and more than twice a length of the third straight section.

2. The tubular needle of claim 1, wherein the first proximal end section further comprises a first curved transitional section extending from the first straight section, such that the second straight section of the second main body section extends from the first curved transitional section; and wherein the second main body section further comprises a second curved transitional section extending from the second straight section, such that the third straight section of the third distal end section extends from the second curved transitional section.

3. The tubular needle of claim 2, wherein the third straight section comprises a plurality of apertures including said aperture, and wherein each of the plurality of apertures face toward said second central axis.

4. The tubular needle of claim 3, wherein the plurality of apertures are present in the third straight section of the tubular side wall such that no aperture is present in the third straight section within 0.2 cm of the blunt closed tip.

5. The tubular needle of claim 3, wherein the first straight section has a length in a range of 0.5 cm to 5.5 cm.

6. The tubular needle of claim 5, wherein the third straight section has a length in a range of 1 cm to 3 cm.

7. The tubular needle of claim 6, wherein the first angle is in a range of 35° to 45°.

8. The tubular needle of claim 7, wherein the second angle is in a range of 15° to 35° and the third angle is in a range of 15° to 25°, such that the fourth composite angle is in a range of 20.8° to 40.0°, such that the third central axis is not coplanar with the first central axis.

9. The tubular needle of claim 1, wherein the first angle is in a range of 35° to 45°; and wherein the second angle is in a range of 15° to 35° and the third angle is in a range of 15° to 25°, such that the fourth composite angle is in a range of 20.8° to 40.0°, such that the third central axis is not coplanar with the first central axis.

10. The tubular needle of claim 1, wherein at least a portion of an exterior surface of the third straight section of the tubular side wall is rougher than a remaining portion of the exterior surface of the tubular side wall, such that an echogenicity of the portion of the exterior surface of the third straight section is higher than the remaining portion of the exterior surface of the tubular side wall.

11. The tubular needle of claim 1, wherein the first straight section has a length in a range of 0.5 cm to 5.5 cm.

12. The tubular needle of claim 11, wherein the third straight section has a length in a range of 1 cm to 3 cm.

13. The tubular needle of claim 12, wherein the first proximal end section further comprises a first curved transitional section extending from the first straight section, such that the second straight section of the second main body section extends from the first curved transitional section; and wherein the second main body section further comprises a second curved transitional section extending from the second straight section, such that the third straight section of the third distal end section extends from the second curved transitional section.

14. The tubular needle of claim 1, further comprising a snare tether extending through the hollow central lumen.

15. The tubular needle of claim 14, further comprising a snare coupled to the snare tether and configured to extend through the aperture.

16. The tubular needle of claim 15, further comprising a light device coupled to the tubular needle on the third straight section.

17. The tubular needle of claim 16, further comprising a second lumen and wherein the light device has a light tether extending from the light device along the second lumen to the proximal end.

18. The tubular needle of claim 1, further comprising a light device coupled to the tubular needle on the third straight section.

19. The tubular needle of claim 18, further comprising a second lumen and wherein the light device has a light tether extending from the light device along the second lumen to the proximal end.

20. The tubular needle of claim 1, wherein the closed blunt tip is detachably attachable to the tubular needle.

* * * * *